US012329892B2

United States Patent
Hobot et al.

(10) Patent No.: US 12,329,892 B2
(45) Date of Patent: Jun. 17, 2025

(54) DEXTROSE CONCENTRATION SENSOR FOR A PERITONEAL DIALYSIS SYSTEM

(71) Applicants: Bellco SRL, Mirandola (IT); MOZARC MEDICAL US LLC, Minneapolis, MN (US)

(72) Inventors: Christopher M Hobot, Rogers, MN (US); Vijaya Kumar Parari, Fridley, MN (US); Fabrizio Puviani, San Felice sul Panaro (IT)

(73) Assignees: MOZARC MEDICAL US LLC, Minneapolis, MN (US); Bellco SRL, Mirandola (IT)

( * ) Notice: Subject to any disclaimer, the term of this patent is extended or adjusted under 35 U.S.C. 154(b) by 770 days.

(21) Appl. No.: 17/404,767

(22) Filed: Aug. 17, 2021

(65) Prior Publication Data
US 2022/0047792 A1 Feb. 17, 2022

Related U.S. Application Data

(63) Continuation-in-part of application No. 17/187,256, filed on Feb. 26, 2021, now Pat. No. 12,194,214, and
(Continued)

(51) Int. Cl.
*A61M 1/28* (2006.01)
*A61M 1/16* (2006.01)

(52) U.S. Cl.
CPC ............ *A61M 1/28* (2013.01); *A61M 1/1609* (2014.02); *A61M 1/1619* (2014.02);
(Continued)

(58) Field of Classification Search
CPC .............. A61M 1/1607; A61M 1/1609; A61M 1/1619; A61M 1/1696; A61M 1/28;
(Continued)

(56) References Cited

U.S. PATENT DOCUMENTS

| 474,732 A | 5/1892 | Gilmore |
|---|---|---|
| 503,226 A | 8/1893 | Anderson |

(Continued)

FOREIGN PATENT DOCUMENTS

| CN | 1273535 | 11/2000 |
|---|---|---|
| CN | 1643368 A | 7/2005 |

(Continued)

OTHER PUBLICATIONS

Brynda, et. al., The detection of toman 2-microglcbuiin by grating coupler immunosensor with three dimensional antibody networks. Biosensors & Bioelectronics, 1999, 363-368, 14(4).
(Continued)

*Primary Examiner* — Dirk R Bass

(57) ABSTRACT

System and methods for sensing fluid characteristics of peritoneal dialysate infused into and removed from a patient during treatment are provided. The systems and methods can use an optical sensor including a transmitter light source operable to emit light through a fluid flow path and an optical receiver operable to receive at least a portion of the light emitted by the transmitter light source.

15 Claims, 4 Drawing Sheets

Related U.S. Application Data a continuation-in-part of application No. 17/024,039, filed on Sep. 17, 2020, now Pat. No. 11,883,576, and a continuation-in-part of application No. 15/673,487, filed on Aug. 10, 2017, now abandoned, said application No. 17/187,256 is a continuation of application No. 15/666,614, filed on Aug. 2, 2017, now Pat. No. 10,994,064, said application No. 17/024,039 is a continuation of application No. 15/666,631, filed on Aug. 2, 2017, now Pat. No. 10,874,790, application No. 17/404,767 is a continuation-in-part of application No. 15/478,569, filed on Apr. 4, 2017, and a continuation-in-part of application No. 15/478,562, filed on Apr. 4, 2017.

(60) Provisional application No. 62/373,133, filed on Aug. 10, 2016, provisional application No. 62/373,225, filed on Aug. 10, 2016, provisional application No. 62/373,228, filed on Aug. 10, 2016, provisional application No. 62/318,169, filed on Apr. 4, 2016, provisional application No. 62/318,173, filed on Apr. 4, 2016, provisional application No. 62/318,183, filed on Apr. 4, 2016.

(52) U.S. Cl.
CPC ... *A61M 1/1696* (2013.01); *A61M 2205/3317* (2013.01); *A61M 2205/3324* (2013.01); *A61M 2205/3327* (2013.01); *A61M 2205/3331* (2013.01); *A61M 2205/3337* (2013.01); *A61M 2205/3368* (2013.01); *A61M 2205/50* (2013.01); *A61M 2205/502* (2013.01); *A61M 2205/52* (2013.01); *A61M 2205/702* (2013.01)

(58) Field of Classification Search
CPC .......... A61M 1/287; A61M 2205/3313; A61M 2205/3317; A61M 2205/3324; A61M 2205/3327; A61M 2205/3331; A61M 2205/3337; A61M 2205/3368; A61M 2205/50; A61M 2205/502; A61M 2205/52; A61M 2205/702; G01N 2021/432; G01N 2021/8542; G01N 2021/8557; G01N 21/4133; G01N 21/431; G01N 21/85
See application file for complete search history.

(56) References Cited

U.S. PATENT DOCUMENTS

| | | |
|---|---|---|
| 564,320 A | 7/1896 | Underwood et al. |
| 3,602,222 A | 8/1971 | Herndon |
| 3,608,729 A | 9/1971 | Haselden |
| 3,669,878 A | 6/1972 | Marantz |
| 3,669,880 A | 6/1972 | Marantz |
| 3,730,183 A | 5/1973 | Goldsmith |
| 3,754,867 A | 8/1973 | Guenther |
| 3,850,835 A | 11/1974 | Marantz |
| 3,884,808 A | 5/1975 | Scott |
| 3,989,622 A | 11/1976 | Marantz |
| 3,989,625 A | 11/1976 | Mason |
| 4,060,485 A | 11/1977 | Eaton |
| 4,371,385 A | 2/1983 | Johnson |
| 4,374,382 A | 2/1983 | Markowitz |
| 4,381,999 A | 5/1983 | Boucher |
| 4,460,555 A | 7/1984 | Thompson |
| 4,556,063 A | 12/1985 | Thompson |
| 4,562,751 A | 1/1986 | Nason |
| 4,581,141 A | 4/1986 | Ash |
| 4,650,587 A | 3/1987 | Polak |
| 4,661,246 A | 4/1987 | Ash |
| 4,678,408 A | 7/1987 | Mason |
| 4,685,903 A | 8/1987 | Cable |
| 4,747,822 A | 5/1988 | Peabody |
| 4,750,494 A | 6/1988 | King |
| 4,772,560 A | 9/1988 | Attar |
| 4,799,493 A | 1/1989 | DuFault |
| 4,826,663 A | 5/1989 | Alberti |
| 4,828,693 A | 5/1989 | Lindsay |
| 4,976,683 A | 12/1990 | Gauthier |
| 5,032,265 A | 7/1991 | Jha |
| 5,080,653 A | 1/1992 | Voss |
| 5,091,642 A | 2/1992 | Chow |
| 5,092,838 A | 3/1992 | Faict |
| 5,092,886 A | 3/1992 | Dobos-Hardy |
| 5,097,122 A | 3/1992 | Coiman |
| 5,127,404 A | 7/1992 | Wyborny |
| 5,141,493 A | 8/1992 | Jacobsen |
| 5,284,470 A | 2/1994 | Beltz |
| 5,302,288 A | 4/1994 | Meidl |
| 5,305,745 A | 4/1994 | Zacouto |
| 5,318,750 A | 6/1994 | Lascombes |
| 5,468,388 A | 11/1995 | Goddard |
| 5,507,723 A | 4/1996 | Keshaviah |
| 5,643,201 A | 7/1997 | Peabody |
| 5,651,893 A | 7/1997 | Kenley |
| 5,683,432 A | 11/1997 | Goedeke |
| 5,744,031 A | 4/1998 | Bene |
| 5,762,782 A | 6/1998 | Kenley |
| 5,819,007 A | 10/1998 | Elghazzawi |
| 5,902,336 A | 5/1999 | Mishkin |
| 5,944,684 A | 8/1999 | Roberts |
| 5,987,352 A | 11/1999 | Klein |
| 6,042,721 A | 3/2000 | Peters |
| 6,048,732 A | 4/2000 | Anslyn |
| 6,052,622 A | 4/2000 | Holmstrom |
| 6,058,331 A | 5/2000 | King |
| 6,156,002 A | 12/2000 | Polaschegg |
| 6,230,059 B1 | 5/2001 | Duffin |
| 6,248,093 B1 | 6/2001 | Moberg |
| 6,254,567 B1 | 7/2001 | Treu |
| 6,321,101 B1 | 11/2001 | Holmstrom |
| 6,362,591 B1 | 3/2002 | Moberg |
| 6,363,279 B1 | 3/2002 | Ben-Haim |
| 6,505,075 B1 | 1/2003 | Weiner |
| 6,554,798 B1 | 4/2003 | Mann |
| 6,555,986 B2 | 4/2003 | Moberg |
| 6,589,229 B1 | 7/2003 | Connelly |
| 6,602,399 B1 | 8/2003 | Fromherz |
| 6,609,023 B1 | 8/2003 | Fischell |
| 6,627,164 B1 | 9/2003 | Wong |
| 6,645,191 B1 | 11/2003 | Knerr |
| 6,676,608 B1 | 1/2004 | Keren |
| 6,689,083 B1 | 2/2004 | Gelfand |
| 6,706,007 B2 | 3/2004 | Gelfand |
| 6,711,439 B1 | 3/2004 | Bradley |
| 6,726,647 B1 | 4/2004 | Sternby |
| 6,758,836 B2 | 7/2004 | Zawacki |
| 6,780,322 B1 | 8/2004 | Bissler |
| 6,818,196 B2 | 11/2004 | Wong |
| 6,878,283 B2 | 4/2005 | Thompson |
| 6,887,214 B1 | 5/2005 | Levin |
| 6,890,315 B1 | 5/2005 | Levin |
| 6,960,179 B2 | 11/2005 | Gura |
| 7,074,332 B2 | 7/2006 | Summerton |
| 7,077,819 B1 | 7/2006 | Goldau |
| 7,131,956 B1 | 11/2006 | Pirazzoli |
| 7,175,809 B2 | 2/2007 | Gelfand |
| 7,207,946 B2 | 4/2007 | Sirokman |
| 7,208,092 B2 | 4/2007 | Micheli |
| 7,276,042 B2 | 10/2007 | Polaschegg |
| 7,399,289 B2 | 7/2008 | Gelfand |
| 7,404,799 B1 | 7/2008 | Koh |
| 7,500,958 B2 | 3/2009 | Asbrink |
| 7,566,432 B2 | 7/2009 | Wong |
| 7,575,564 B2 | 8/2009 | Childers |
| 7,610,086 B1 | 10/2009 | Ke |
| 7,674,231 B2 | 3/2010 | McCombie |
| 7,704,361 B2 | 4/2010 | Garde |
| 7,736,507 B2 | 6/2010 | Wong |

(56) References Cited

U.S. PATENT DOCUMENTS

| | | |
|---|---|---|
| 7,744,553 B2 | 6/2010 | Kelly |
| 7,754,852 B2 | 7/2010 | Burnett |
| 7,756,572 B1 | 7/2010 | Fard |
| 7,775,983 B2 | 8/2010 | Zhang |
| 7,775,986 B2 | 8/2010 | Roeher |
| 7,776,210 B2 | 8/2010 | Rosenbaum |
| 7,785,463 B2 | 8/2010 | Bissler |
| 7,794,141 B2 | 9/2010 | Perry |
| 7,850,635 B2 | 12/2010 | Polaschegg |
| 7,857,976 B2 | 12/2010 | Bissler |
| 7,867,214 B2 | 1/2011 | Childers |
| 7,896,831 B2 | 3/2011 | Sternby |
| 7,922,686 B2 | 4/2011 | Childers |
| 7,922,911 B2 | 4/2011 | Micheli |
| 7,947,179 B2 | 5/2011 | Rosenbaum |
| 7,955,291 B2 | 6/2011 | Sternby |
| 7,967,022 B2 | 6/2011 | Grant |
| 7,981,082 B2 | 7/2011 | Wang |
| 8,000,000 B2 | 8/2011 | Greenberg |
| 8,034,161 B2 | 10/2011 | Gura |
| 8,070,709 B2 | 12/2011 | Childers |
| 8,096,969 B2 | 1/2012 | Roberts |
| 8,105,260 B2 | 1/2012 | Tonelli |
| 8,183,046 B2 | 5/2012 | Lu |
| 8,187,250 B2 | 5/2012 | Roberts |
| 8,197,439 B2 | 6/2012 | Wang |
| 8,202,241 B2 | 6/2012 | Karakama |
| 8,246,826 B2 | 8/2012 | Wilt |
| 8,273,049 B2 | 9/2012 | Demers |
| 8,282,828 B2 | 10/2012 | Wallenas |
| 8,292,594 B2 | 10/2012 | Tracey |
| 8,313,642 B2 | 11/2012 | Yu |
| 8,317,492 B2 | 11/2012 | Demers |
| 8,357,113 B2 | 1/2013 | Childers |
| 8,366,316 B2 | 2/2013 | Kamen |
| 8,366,655 B2 | 2/2013 | Kamen |
| 8,394,601 B2 | 3/2013 | Klein |
| 8,404,091 B2 | 3/2013 | Ding |
| 8,409,441 B2 | 4/2013 | Wilt |
| 8,496,809 B2 | 7/2013 | Roger |
| 8,499,780 B2 | 8/2013 | Wilt |
| 8,500,676 B2 | 8/2013 | Jansson |
| 8,512,271 B2 | 8/2013 | Moissl |
| 8,518,260 B2 | 8/2013 | Raimann |
| 8,521,482 B2 | 8/2013 | Akonur |
| 8,535,525 B2 | 9/2013 | Heyes |
| 8,560,510 B2 | 10/2013 | Brueggerhoff |
| 8,580,112 B2 | 11/2013 | Updyke |
| 8,597,227 B2 | 12/2013 | Childers |
| 8,696,626 B2 | 4/2014 | Kirsch |
| 8,903,492 B2 | 12/2014 | Soykan |
| 8,926,542 B2 | 1/2015 | Gerber |
| 9,700,663 B2 | 7/2017 | Burbank |
| 9,907,897 B2 | 3/2018 | Burbank |
| 10,046,100 B2 | 8/2018 | Burbank |
| 10,076,599 B2 | 9/2018 | Eyrard |
| 10,076,735 B2 | 9/2018 | Jansson |
| 10,172,992 B2 | 1/2019 | Neftel |
| 10,173,881 B2 | 1/2019 | Beavis |
| 10,459,459 B2 | 10/2019 | Beavis |
| 10,478,544 B2 | 11/2019 | Friederichs |
| 10,610,630 B2 | 4/2020 | Burbank |
| 2002/0016550 A1 | 2/2002 | Sweeney |
| 2002/0042561 A1 | 4/2002 | Schulman |
| 2002/0112609 A1 | 8/2002 | Wong |
| 2003/0028089 A1 | 4/2003 | Galley |
| 2003/0069481 A1 | 4/2003 | Hervy |
| 2003/0080059 A1 | 5/2003 | Peterson |
| 2003/0097086 A1 | 5/2003 | Gura |
| 2003/0105435 A1 | 6/2003 | Taylor |
| 2003/0113931 A1 | 6/2003 | Pan |
| 2003/0114787 A1 | 6/2003 | Gura |
| 2003/0187479 A1 | 10/2003 | TranThong |
| 2004/0019312 A1 | 1/2004 | Childers |
| 2004/0060865 A1 | 4/2004 | Callan |
| 2004/0068219 A1 | 4/2004 | Summerton |
| 2004/0099593 A1 | 5/2004 | DePaolis |
| 2004/0121982 A1 | 6/2004 | Martis |
| 2004/0147900 A1 | 7/2004 | Polaschegg |
| 2004/0168969 A1 | 9/2004 | Sternby |
| 2004/0215090 A1 | 10/2004 | Erkkila |
| 2005/0065760 A1 | 3/2005 | Murtfeldt |
| 2005/0113796 A1 | 5/2005 | Taylor |
| 2005/0126961 A1 | 6/2005 | Bissler |
| 2005/0131331 A1 | 6/2005 | Kelly |
| 2005/0126998 A1 | 7/2005 | Childers |
| 2005/0150832 A1 | 7/2005 | Tsukamoto |
| 2005/0214863 A1 | 9/2005 | McDevitt |
| 2005/0234354 A1 | 10/2005 | Rowlandson |
| 2005/0234357 A1 | 10/2005 | Xue |
| 2005/0234381 A1 | 10/2005 | Niemetz |
| 2005/0234534 A1 | 10/2005 | Rowlandson |
| 2005/0236330 A1 | 10/2005 | Nier |
| 2005/0265895 A1 | 12/2005 | Kopelman |
| 2005/0274658 A1 | 12/2005 | Rosenbaum |
| 2006/0025661 A1 | 2/2006 | Sweeney |
| 2006/0025748 A1 | 2/2006 | Ye |
| 2006/0217771 A1 | 2/2006 | Soykan |
| 2006/0058731 A1 | 3/2006 | Burnett |
| 2006/0191850 A1 | 8/2006 | Bosetto |
| 2006/0195064 A1 | 8/2006 | Plahey |
| 2006/0226079 A1 | 10/2006 | Mori |
| 2006/0241709 A1 | 10/2006 | Soykan |
| 2006/0247548 A1 | 11/2006 | Sarkar |
| 2006/0264894 A1 | 11/2006 | Moberg |
| 2007/0007208 A1 | 1/2007 | Brugger |
| 2007/0038138 A1 | 2/2007 | Gill |
| 2007/0066928 A1 | 3/2007 | Lannoy |
| 2007/0073168 A1 | 3/2007 | Zhang |
| 2007/0138011 A1 | 6/2007 | Hofmann |
| 2007/0161113 A1 | 7/2007 | Ash |
| 2007/0175827 A1 | 8/2007 | Wariar |
| 2007/0179431 A1 | 8/2007 | Roberts |
| 2007/0213653 A1 | 9/2007 | Childers |
| 2007/0215545 A1 | 9/2007 | Bissler |
| 2007/0255250 A1 | 11/2007 | Moberg |
| 2007/0276270 A1 | 11/2007 | Tran |
| 2008/0006570 A1 | 1/2008 | Gura |
| 2008/0015487 A1 | 1/2008 | Szamosfalvi |
| 2008/0021337 A1 | 1/2008 | Li |
| 2008/0053905 A9 | 3/2008 | Brugger |
| 2008/0067132 A1 | 3/2008 | Ross |
| 2008/0093276 A1 | 4/2008 | Roger |
| 2008/0200866 A1 | 8/2008 | Prisco |
| 2008/0215247 A1 | 9/2008 | Tonelli |
| 2008/0253427 A1 | 10/2008 | Kamen |
| 2009/0007642 A1 | 1/2009 | Busby |
| 2009/0020471 A1 | 1/2009 | Tsukamoto |
| 2009/0036825 A1 | 2/2009 | Petersen |
| 2009/0101577 A1 | 4/2009 | Fulkerson |
| 2009/0124869 A1 | 5/2009 | Hu |
| 2009/0124963 A1 | 5/2009 | Hogard |
| 2009/0127193 A1 | 5/2009 | Updyke |
| 2009/0149776 A1 | 6/2009 | Adams |
| 2009/0171261 A1 | 7/2009 | Sternby |
| 2009/0264776 A1 | 10/2009 | Vardy |
| 2009/0275849 A1 | 11/2009 | Stewart |
| 2009/0275883 A1 | 11/2009 | Chapman |
| 2009/0281484 A1 | 11/2009 | Childers |
| 2009/0282980 A1 | 11/2009 | Gura |
| 2009/0314063 A1 | 12/2009 | Sternby |
| 2010/0004588 A1 | 1/2010 | Yeh |
| 2010/0010425 A1 | 1/2010 | Yu |
| 2010/0010429 A1 | 1/2010 | Childers |
| 2010/0042035 A1 | 2/2010 | Moissl |
| 2010/0076398 A1 | 3/2010 | Scheurer |
| 2010/0078381 A1 | 4/2010 | Merchant |
| 2010/0078387 A1 | 4/2010 | Wong |
| 2010/0084330 A1 | 4/2010 | Wong |
| 2010/0087771 A1 | 4/2010 | Karakama |
| 2010/0094158 A1 | 4/2010 | Solem |
| 2010/0113891 A1 | 5/2010 | Barrett |
| 2010/0114012 A1 | 5/2010 | Sandford |
| 2010/0137693 A1 | 6/2010 | Porras |

(56) References Cited

U.S. PATENT DOCUMENTS

| | | |
|---|---|---|
| 2010/0137782 A1 | 6/2010 | Jansson |
| 2010/0168546 A1 | 7/2010 | Kamath |
| 2010/0217180 A1 | 8/2010 | Akonur |
| 2010/0217181 A1 | 8/2010 | Roberts |
| 2010/0224492 A1 | 9/2010 | Ding |
| 2010/0234795 A1 | 9/2010 | Wallenas |
| 2010/0241045 A1 | 9/2010 | Kelly |
| 2010/0264086 A1 | 10/2010 | Noack |
| 2010/0312172 A1 | 12/2010 | Hoffman |
| 2011/0017665 A1 | 1/2011 | Updyke |
| 2011/0048949 A1 | 3/2011 | Ding et al. |
| 2011/0066006 A1 | 3/2011 | Banet |
| 2011/0066043 A1 | 3/2011 | Banet |
| 2011/0071465 A1 | 3/2011 | Wang |
| 2011/0077574 A1 | 3/2011 | Sigg |
| 2011/0077575 A1 | 3/2011 | Kraemer |
| 2011/0079558 A1 | 4/2011 | Raimann |
| 2011/0081728 A1 | 4/2011 | Putnam |
| 2011/0087187 A1 | 4/2011 | Beck |
| 2011/0100909 A1 | 5/2011 | Stange |
| 2011/0106003 A1 | 5/2011 | Childers |
| 2011/0130666 A1 | 6/2011 | Dong |
| 2011/0137136 A1 | 6/2011 | Kotanko |
| 2011/0141116 A1 | 6/2011 | Dalesch |
| 2011/0144570 A1 | 6/2011 | Childers |
| 2011/0184340 A1 | 7/2011 | Tan |
| 2011/0208105 A1 | 8/2011 | Brandl |
| 2011/0272337 A1 | 11/2011 | Palmer |
| 2011/0301447 A1 | 12/2011 | Park |
| 2011/0301472 A1 | 12/2011 | Grober |
| 2012/0016228 A1 | 1/2012 | Kroh |
| 2012/0029937 A1 | 2/2012 | Neftel |
| 2012/0083729 A1 | 4/2012 | Childers |
| 2012/0085707 A1 | 4/2012 | Beiriger |
| 2012/0115248 A1 | 5/2012 | Ansyln |
| 2012/0135396 A1 | 5/2012 | McDevitt |
| 2012/0181230 A1 | 7/2012 | Kloeffel |
| 2012/0220528 A1 | 8/2012 | VanAntwerp |
| 2012/0258545 A1 | 10/2012 | Ash |
| 2012/0258546 A1 | 10/2012 | Marran |
| 2012/0259276 A1 | 10/2012 | Childers |
| 2012/0273354 A1 | 11/2012 | Orhan |
| 2012/0273415 A1 | 11/2012 | Gerber |
| 2012/0273420 A1 | 11/2012 | Gerber |
| 2012/0277546 A1 | 11/2012 | Soykan |
| 2012/0277551 A1 | 11/2012 | Gerber |
| 2012/0277552 A1 | 11/2012 | Gerber |
| 2012/0277604 A1 | 11/2012 | Gerber |
| 2012/0277650 A1 | 11/2012 | Gerber |
| 2012/0277655 A1 | 11/2012 | Gerber |
| 2012/0277722 A1 | 11/2012 | Gerber |
| 2012/0283581 A1 | 11/2012 | Olde et al. |
| 2012/0303079 A1 | 11/2012 | Mahajan |
| 2013/0037465 A1 | 2/2013 | Heyes |
| 2013/0062265 A1 | 3/2013 | Balschat |
| 2013/0116578 A1 | 5/2013 | QiAn |
| 2013/0158461 A1 | 6/2013 | Sasaki |
| 2013/0168316 A1 | 7/2013 | Noguchi |
| 2013/0186759 A1 | 7/2013 | Lin |
| 2013/0193073 A1 | 8/2013 | Hogard |
| 2013/0199998 A1 | 8/2013 | Kelly |
| 2013/0211730 A1 | 8/2013 | Wolff |
| 2013/0213890 A1 | 8/2013 | Kelly |
| 2013/0228517 A1 | 9/2013 | Roger |
| 2013/0231607 A1 | 9/2013 | Roger |
| 2013/0248426 A1 | 9/2013 | Pouchoulin |
| 2013/0263650 A1* | 10/2013 | Nier .................. A61M 1/1654 73/61.46 |
| 2013/0274642 A1 | 10/2013 | Soykan |
| 2013/0324915 A1 | 12/2013 | (Krensky)Britton |
| 2013/0330208 A1 | 12/2013 | Ly |
| 2013/0331774 A1 | 12/2013 | Farrell |
| 2014/0018727 A1 | 1/2014 | Burbank |
| 2014/0018728 A1 | 1/2014 | Plahey |
| 2014/0042092 A1 | 2/2014 | Akonur |
| 2014/0065950 A1 | 3/2014 | Mendelsohn |
| 2014/0088442 A1 | 3/2014 | Soykan |
| 2014/0276375 A1 | 3/2014 | Minkus |
| 2014/0110340 A1 | 4/2014 | White |
| 2014/0110341 A1 | 4/2014 | White |
| 2014/0158538 A1 | 6/2014 | Collier |
| 2014/0158588 A1 | 6/2014 | Pudil |
| 2014/0158623 A1 | 6/2014 | Pudil |
| 2014/0190876 A1 | 7/2014 | Meyer |
| 2014/0216250 A1 | 8/2014 | Meyer |
| 2014/0217028 A1 | 8/2014 | Pudil |
| 2014/0217029 A1 | 8/2014 | Meyer |
| 2014/0217030 A1 | 8/2014 | Meyer |
| 2014/0220699 A1 | 8/2014 | Pudil |
| 2014/0314625 A1 | 10/2014 | Clift |
| 2015/0032023 A1 | 1/2015 | Soykan |
| 2015/0080682 A1 | 3/2015 | Gerber |
| 2015/0088047 A1 | 3/2015 | Gerber |
| 2015/0141512 A1 | 5/2015 | Kizhakkedathu |
| 2015/0144539 A1 | 5/2015 | Pudil |
| 2015/0148697 A1 | 5/2015 | Burnes |
| 2015/0149096 A1 | 5/2015 | Soykan |
| 2015/0250427 A1 | 9/2015 | Soykan |
| 2015/0343126 A1 | 12/2015 | Merchant |
| 2015/0352269 A1 | 12/2015 | Gerber |
| 2015/0367054 A1 | 12/2015 | Gerber |
| 2016/0018347 A1 | 1/2016 | Drbal |
| 2016/0023467 A1 | 2/2016 | Smith |
| 2016/0143774 A1 | 5/2016 | Burnett |
| 2016/0166753 A1 | 6/2016 | Meyer |
| 2016/0206801 A1 | 7/2016 | Gerber |
| 2016/0331884 A1 | 11/2016 | Sigg |
| 2017/0319768 A1 | 11/2017 | Szpara |
| 2018/0043080 A1 | 2/2018 | Gerber |
| 2018/0221555 A1 | 8/2018 | Rohde |
| 2019/0125952 A1 | 5/2019 | Jansson |
| 2019/0125954 A1 | 5/2019 | Mathiot |
| 2019/0151526 A1 | 5/2019 | Wieslander |
| 2019/0240389 A1 | 8/2019 | Rohde |

FOREIGN PATENT DOCUMENTS

| | | |
|---|---|---|
| CN | 101193667 | 6/2008 |
| CN | 101300476 A | 11/2008 |
| CN | 201342127 | 11/2009 |
| CN | 202048893 | 3/2011 |
| CN | 103037917 | 4/2013 |
| CN | 103394139 | 11/2013 |
| CN | 103619372 | 3/2014 |
| CN | 103751871 | 4/2014 |
| CN | 103717132 | 9/2014 |
| CN | 104174077 | 12/2014 |
| CN | 104271173 | 1/2015 |
| CN | 104833635 A | 8/2015 |
| CN | 104884102 | 9/2015 |
| CN | 105008893 B | 10/2015 |
| CN | 105142692 | 12/2015 |
| CN | 105692957 A | 6/2016 |
| CN | 205672288 | 11/2016 |
| CN | 107206147 | 9/2017 |
| DE | 3224823 | 1/1984 |
| DE | 102006028172 A1 | 12/2017 |
| EP | 0266795 A2 | 11/1987 |
| EP | 0402505 | 12/1990 |
| EP | 0272414 | 10/1991 |
| EP | 0330892 | 7/1994 |
| EP | 1175238 | 11/2000 |
| EP | 1085295 | 11/2001 |
| EP | 1281351 | 2/2003 |
| EP | 2308526 | 10/2003 |
| EP | 1364666 A1 | 11/2003 |
| EP | 1523347 | 1/2004 |
| EP | 1523350 | 1/2004 |
| EP | 0906768 B1 | 2/2004 |
| EP | 1691863 | 4/2005 |
| EP | 2116269 | 2/2008 |
| EP | 1450879 | 10/2008 |
| EP | 1514562 | 4/2009 |
| EP | 2219703 | 5/2009 |

(56) References Cited

FOREIGN PATENT DOCUMENTS

| | | |
|---|---|---|
| EP | 1592494 B1 | 6/2009 |
| EP | 2398529 | 11/2010 |
| EP | 2575827 A2 | 12/2010 |
| EP | 2100553 | 8/2011 |
| EP | 2576453 A2 | 12/2011 |
| EP | 2701580 | 11/2012 |
| EP | 2701595 | 11/2012 |
| EP | 1345856 B1 | 3/2013 |
| EP | 2344220 B1 | 4/2013 |
| EP | 1351756 | 7/2013 |
| EP | 2190498 | 7/2013 |
| EP | 2701596 | 3/2014 |
| EP | 1582226 | 1/2016 |
| JP | S55138462 | 10/1980 |
| JP | S63-143077 | 11/1987 |
| JP | 2002533170 | 10/2002 |
| JP | 2002542900 | 12/2002 |
| JP | 2003235965 | 8/2003 |
| JP | 2005-533573 | 11/2005 |
| JP | 5-99464 | 10/2012 |
| WO | WO1992005814 | 4/1992 |
| WO | 1995003839 | 2/1995 |
| WO | WO 1998054563 | 12/1998 |
| WO | WO1999006082 | 2/1999 |
| WO | 9937342 | 7/1999 |
| WO | 0057935 | 10/2000 |
| WO | 2000066197 | 11/2000 |
| WO | 200170307 A1 | 9/2001 |
| WO | 2001085295 A2 | 9/2001 |
| WO | 0185295 A2 | 11/2001 |
| WO | 2002013691 | 2/2002 |
| WO | WO 20020053211 | 7/2002 |
| WO | 2003043677 A2 | 5/2003 |
| WO | 2003043680 | 5/2003 |
| WO | 2003051422 A2 | 6/2003 |
| WO | 2004008826 | 1/2004 |
| WO | 2004009156 | 1/2004 |
| WO | 2004009158 | 1/2004 |
| WO | 2004030716 A2 | 4/2004 |
| WO | 2004030717 A2 | 4/2004 |
| WO | 2004064616 A2 | 8/2004 |
| WO | 2005033701 | 4/2005 |
| WO | 2005061026 | 7/2005 |
| WO | 2005123230 A2 | 12/2005 |
| WO | 2006011009 | 2/2006 |
| WO | 2006017446 | 2/2006 |
| WO | 2007038347 | 4/2007 |
| WO | 2007089855 A2 | 8/2007 |
| WO | WO2009094035 A1 | 1/2008 |
| WO | 2008037410 | 4/2008 |
| WO | 2009026603 | 12/2008 |
| WO | 2009024566 | 2/2009 |
| WO | 2009061608 | 5/2009 |
| WO | 2009094184 | 7/2009 |
| WO | 2009157877 A1 | 12/2009 |
| WO | 2009157878 A1 | 12/2009 |
| WO | WO2009154955 A2 | 12/2009 |
| WO | WO 20090154955 | 12/2009 |
| WO | 2010024963 | 3/2010 |
| WO | 2010028860 | 3/2010 |
| WO | 2010033314 | 3/2010 |
| WO | 2010033699 | 3/2010 |
| WO | 2010077851 | 7/2010 |
| WO | WO 20100002830 | 7/2010 |
| WO | 2010096659 | 10/2010 |
| WO | 2010121820 | 10/2010 |
| WO | 2011025705 A1 | 3/2011 |
| WO | 2011026645 | 3/2011 |
| WO | WO2013022760 A1 | 8/2011 |
| WO | WO 2011/132046 | 10/2011 |
| WO | 2011137693 | 11/2011 |
| WO | WO2011161056 | 12/2011 |
| WO | 2012042323 | 4/2012 |
| WO | 2012050781 | 4/2012 |
| WO | 2012051996 | 4/2012 |
| WO | 2012073420 | 7/2012 |
| WO | WO 2012/129501 | 9/2012 |
| WO | 2012148781 | 11/2012 |
| WO | 2012148784 | 11/2012 |
| WO | 2012148786 | 11/2012 |
| WO | 2012148787 A1 | 11/2012 |
| WO | 2012148789 | 11/2012 |
| WO | 2012162515 A2 | 11/2012 |
| WO | WO2012148788 A1 | 11/2012 |
| WO | WO 20120148784 | 11/2012 |
| WO | 2012172398 | 12/2012 |
| WO | 2013019179 A1 | 2/2013 |
| WO | 2013019994 A2 | 2/2013 |
| WO | 2013025844 | 2/2013 |
| WO | 2013028809 A3 | 2/2013 |
| WO | 2013101292 | 7/2013 |
| WO | 2013103607 A1 | 7/2013 |
| WO | 2013103906 | 7/2013 |
| WO | 2013110906 | 8/2013 |
| WO | 2013110919 | 8/2013 |
| WO | 2013114063 A1 | 8/2013 |
| WO | 2013121162 A1 | 8/2013 |
| WO | 2013140346 | 9/2013 |
| WO | 2013141896 | 9/2013 |
| WO | WO 20140121161 | 1/2014 |
| WO | 14066254 | 5/2014 |
| WO | 14066255 | 5/2014 |
| WO | 14077082 | 5/2014 |
| WO | 2014121162 | 8/2014 |
| WO | 2014121163 | 8/2014 |
| WO | 2014121167 | 8/2014 |
| WO | 2014121169 | 8/2014 |
| WO | WO2014121161 | 8/2014 |
| WO | WO2015081221 A1 | 6/2015 |
| WO | WO 20150130205 | 9/2015 |
| WO | WO 20150159280 | 10/2015 |
| WO | WO2016049542 | 3/2016 |
| WO | WO 20160080883 | 5/2016 |
| WO | WO 20170034452 | 3/2017 |
| WO | WO 2017/176687 | 10/2017 |
| WO | WO 2017/176701 | 10/2017 |
| WO | WO2018229125 | 12/2018 |

OTHER PUBLICATIONS

Wheaton, et al., Dowex Ion Exchange Resins—Fundamentals of Ion Exchange; Jun. 2000, pp. 1-9. http://www.dow.com/scripts/litorder.asp?filepath=liquidseps/pdfs/noreg/177-01837.pdf.

Zhong, et. al., Miniature urea sensor based on H(+)-ion sensitive field effect transistor and its application in clinical analysis, Chin. J. Biotechnol., 1992, 57-65. 8(1).

PCT/US2012/034331, International Search Report and Written Opinion dated Jul. 9, 2012.

Roberts M, The regenerative dialysis (REDY) sorbent system. Nephrology, 1998, 275-278:4.

Hemametrics, Crit-Line Hematocrit Accuracy, 2003, 1-5, vol. 1, Tech Note No. 11 (Rev. D).

Weissman, S., et al., Hydroxyurea-induced hepatitis in human immunodeficiency virus-positive patients. Clin. Infec. Dis, (Jul. 29, 1999): 223-224.

PCT/US2012/034334, International Search Report, Jul. 6, 2012.
PCT/US2012/034335, International Search Report, Sep. 5, 2012.
PCT/US/2012/034327, International Search Report, Aug. 13, 2013.
PCT/US/2012/034329, International Search Report, Dec. 3, 2012.

Foley, et al., Long Interdialytic Interval and Martality among Patients Receiving Hemodialysis, N Engl Jrnl Med. 2011:365(12):1099-1107.

PCT International Search Report from International Application No. PCT/US2014/067650, dated Mar. 9, 2015.

Wang, Fundamentals of intrathoracic impedance monitoring in heart failure, Am. J. Cardiology, 2007, 3G-10G: Suppl.

PCT/US2014/067650 International Search Report Written Opinion mailed Mar. 9, 2015.

Bleyer, et al, Kidney International. Jun. 2006; 69(12):2268-2273.

Bleyer, et. al., Sudden and cardiac death rated in hemodialysis patients, Kidney International. 1999, 1553-1559: 55.

(56) References Cited

OTHER PUBLICATIONS

PCT/US2012/034335, International Preliminary Report on Patentability, Oct. 29, 2013.
PCT/US2012/034303, Internationa Search Report, Jul. 6, 2013.
PCT/US2012/034332, Internatonal Preliminary Report on Patentability, Oct. 29, 2013.
PCT/US2012/034333, International Preliminary Report on Patentability, Oct. 29, 2013.
PCT/US2012/034333, International Search Report, Aug. 29, 2012.
PCT/US2012/034327, International Preliminary Report on Patentability, Oct. 29, 2013.
PCT/US2012/034330, International Preliminary Report on Patentability, Oct. 29, 2013.
Culleton, BF et al. Effect of Frequent Nocturnal Hemodialysis vs. Conventional Hemodialysis on Left Ventricular Mass and Quality of Life. 2007 Journal of the American Medical Association 298 (11), 1291-1299.
Redfield, et. al., Restoration of renal response to atria! natriuretic factor in experimental low-output heat failure, Am. J. Physiol., Oct. 1, 1989, R917-923:257.
Rogoza, et. al., Validation of A&D UA-767 device for the self-measurement of blood pressure, Blood Pressure Monitoring, 2000, 227-231, 5(4).
PCT/US2012/034329, International Preliminary Report on Patentability, Oct. 29, 2013.
Lima, et. al., An electrochemical sensor based on nanostructure hollandite-type manganese oxide for detection of potassium ion, Sensors, Aug. 24, 2009, 6613-8625, 9.
Maclean, et, al., Effects of hindlimb contraction on pressor and muscle interstitial metabolite responses in the cat, J. App. Physiol., 1998, 1583-1592, 85(4).
PCT/US2014/014357 International Search Report and Written Opinion dated May 19, 2014.
PCT/US2014/014357 International Search Report and Written Opinion mailed May 19, 2014.
Ronco et al. 2008, Cardiorenal Syndrome, Journal American College Cardiology, 52:1527-1539, Abstract.
Overgaard, et. al., Activity-induced recovery of excitability in K+-depressed rat soleus muscle, Am. J. p. 280: R48-R55, Jan. 1, 2001.
Overgaard. et. al., Relations between excitability and contractility in rate soleusmuscle: role of the Na+—K+ pump and Na+—K—S gradients. Journal of Physiology, 1999, 215-225, 518(1).
Zoccali, Pulmonary Congestion Predicts Cardiac Events and Mortality in ESRD, Clinical Epidemiology, J. Am Soc Nephrol 24:639-646, 2013.
Coast, et al. 1990, An approach to Cardiac Arrhythmia analysis Using Hidden Markov Models, IEEE Transactions On Biomedical Engineering. 1990, 37(9):826-835.
Weiner, et. al., Article: Cardiac Function and Cardiovascular Disease in Chronic Kidney Disease, Book: Primer on Kidney Diseases (Author: Greenberg, et al), 2009,499-505, 5th Ed., Saunders Elsevier, Philadelphia, PA.
Velasco, Optimal Fluid Control can Normalize Cardiovascular Risk Markers and Limit Left Ventricular Hypertrophy in Thrice Weekly Dialysis Patients, Hemodialysis Intenational, 16:465-472, 2012.
Whitman, CKD and Sudden Cardiac Death: Epidemiology, Mechanisms, and Therapeutic Approaches, J Am Soc Nephrol, 23:1929-1939, 2012.
Hall, Hospitalization for Congestive Heart Failure: United States, 2000-2010, NCHS Data Brief, No. 108, Oct. 2012.
Albert, Fluid Management Strategies in Heart Failure, Critical Care Nurse, 32:20-32, 2012.
PCT/US2014/065201 International Search Report mailed May 26, 2015.
Genovesi, et al., Nephrology, Dialysis, Transplantation 2009; 24(8):2529-2536.
Secemsky, et. al, High prevalence of cardiac autonomic dysfunction and T-wave alternans in dialysis patients. Heart Rhythm, Apr. 2011, 592-598 : vol. 8, No. 4.
Wei, et. al., Fullerene-cryptand coated piezoelectric crystal urea sensor based on urease, Analytica Chimica Acta, 2001,77-85:437.
Gambro AK 96 Dialysis Machine Operators Manual, Dec. 2012. p. 1-140.
Gambro AK 96 Dialysis Machine Operators Manual, Dec. 2012. p. 141-280.
Gambro AK 96 Dialysis Machine Operators Manual, Dec. 2012. p. 281-420.
Gambro AK 96 Dialysis Machine Operators Manual, Dec. 2012. p. 421-534.
Leifer et al., A Study on the Temperature Variation of Rise Velocity for Large Clean Bubbles, J. Atmospheric & Oceanic Tech., vol. 17, pp. 1392-1402, Oct. 2000.
Talaia, Terminal Velocity of a Bubble Rise in a Liquid Column, World Acad. of Sci., Engineering & Tech., vol. 28, pp. 264-268, Published Jan. 1, 2007.
The FHN Trial Group. In-Center. Hemodialysis Six Times per Week versus Three Times per Week, New England Journal of Medicine, 2010 Abstract.
PCT/US2012/034332, International Search Report, Jul. 5, 2012.
Siegenthaler, et al., Pulmonary fluid status monitoring with intrathoracic impedance, Journal of Clinical Monitoring and Computing, 24:449-451, published Jan. 12, 2011.
John Wm Agar: Review: Understanding sorbent dialysis systems, Nephrology, vol. 15, No. 4, Jun. 1, 2010, pp. 406-411.
European Office Action in Application 12717020.7 dated Sep. 14, 2016.
Lakerveld et al, Primary prevention of diabetes mellitus type 2 and cardiovascular diseases using a cognitive behavior program aimed at lifestyle changes in people at risk: Design of a randomized controlled trial, 2008, BMC Endocrine Disorders, 8(6): 1-19.
Gordhandas et al, Real-Time Extraction and Analysis of Key Morphological Features in the Electrocardiogram, for Data Compression and Clinical Decision Support, 2004, Computational Physiology, pp. 15-18.
European Office Action in Application 12717020.7 dated Dec. 11, 2015.
PCT/US2012/034331 International Preliminary Report on Patentability and Written Opinion dated Oct. 29, 2013.
Office Action in Chinese Application No. 201280020932.1 Dated Jan. 7, 2015.
Office Action in Chinese Application No. 201280020932.1 Dated Apr. 3, 2015.
PCT/US2012/034330, International Search Report and Written Opinion dated Aug. 28, 2012.
Office Action in Chinese Application No. 201280020937.4 dated Mar. 22, 2016.
Office Action in Japanese Application No. 2014-508434 dated Nov. 16, 2015.
Office Action in Japanese Application No. 2014-508434 dated Dec. 8, 2014.
Office Action in Japanese Application No. 2014-508434 dated Nov. 4, 2016.
Office Action in European Application No. 12717019.9 dated Feb. 16, 2017.
Office Action in Chinese Application No. 201510511657.9 dated May 10, 2017.
PCT/US2014/065201 International Preliminary Report on Patentability mailed May 19, 2016.
Office Action in European Application No. EP 12717021.5 dated Feb. 3, 2017.
Office Action in Chinese Application No. 201510593695.3 dated Jul. 12, 2017.
Office Action in European Application No. EP 12719170.8 dated Jan. 14, 2015.
Office Action in Japanese Application No. JP 2014-508437 dated Dec. 8, 2014.
U.S. Appl. No. 60/650,497 dated Feb. 7, 2005.
Nedelkov, et. al., Design of buffer exchange surfaces and sensor chips for biosensor chip mass spectrometry, Proteomics, 2002, 441-446, 2(4).
European Search Report App 14865374.4, Jun. 12, 2017.

(56) References Cited

OTHER PUBLICATIONS

European Search Report for Application No. 14865128.4 dated Jun. 20, 2017.
Green et al., Sudden Cardiac Death in Hemodialysis Patients: an In-Depth Review, Am J Kidney Dis 57(6)921:929; published Apr. 18, 2011.
Rajan et al. Generalized Feature Extraction for Time-Varying Autoregressive Models, IEEE Transacion Signal Processing vol. 44, No. 10; published Oct. 1, 1996.
AU Examiners Report for Application No. 2017246829, dated Jan. 9, 2021.
Castellanos, et al, Clinical Relevance of Intraperitoneal Pressure in Peritoneal Dialysis Patients, Perit Dial Int. Sep.-Oct. 2017;37(5):562-567. doi: 10.3747/pdi.2016.00267. Epub Jul. 11, 2017.
Chinese OA in 201710669452.2 of Oct. 16, 2019.
Chinese Office Action for App. No. 201710669451.8, dated Jun. 2, 2020.
Chinese Office Action for App. No. 201710669451.8, dated Sep. 12, 2019.
Chinese Office Action for App. No. 201710669452.2, dated Dec. 3, 2019.
Chinese Office Action for App. No. 201710669454.1, dated Feb. 25, 2020.
Chinese Office Action for App. No. 201710669454.1, dated Jul. 3, 2020.
Chinese Office Action for App. No. 201710778666.3, dated Jul. 15, 2020.
Chinese Office Action for App. No. 201780019237.6, dated Feb. 1, 2021.
Chinese Office Action for App. No. 201780019237.6, dated May 25, 2020.
Chinese Office Action for App. No. 201780019238.0, dated May 7, 2020.
Chinese Office Action for App. No. 201780019362.7, dated Jun. 2, 2020.
Chinese Office Action for App. No. 201811107614.4, dated Sep. 28, 2020.
Chinese Office Action for App. No. 201811155891.2, dated Oct. 10, 2020.
Chinese Office Action for App. No. 2019071601874110, dated Jul. 19, 2019.
Chinese Office Action for Application No. 201811096062.1, dated Mar. 19, 2021.
Chinese Office Action in App. No. 201480059332.5, Dated Mar. 30, 2018.
Chinese Office Action in App. No. 201710669452.2, dated May 11, 2020.
Dejardin, et al, Intraperitoneal pressure in PD patients: relationship to intraperitoneal volume, body size and PD-related complications, Nephrol Dial Transplant. May 2007;22(5):1437-44.
European Office Action for App. No. 12719842.2, dated Jul. 15, 2020.
European Office Action for App. No. 14859115.9, dated Mar. 25, 2020.
European Office Action for App. No. 17718246.6, dated Apr. 2, 2020.
European Office Action for App. No. 17754582.9, dated Aug. 10, 2020.
European Search Report for App. No. 17185636.2, Dated Mar. 27, 2018.
European Search Report for App. No. 14859115.9, dated Jan. 5, 2018.
European Search Report for App. No. 17185636.2 dated Jan. 10, 2018.
European Search Report for App. No. 17185638.8, dated Dec. 19, 2017.
European Search Report for App. No. 17185808.7, dated Jan. 2, 2018.
European Search Report for App. No. 17185810.3, dated Dec. 15, 2017.
European Search Report for App. No. 17190053.3, dated Jan. 2, 2018.
European Search Report for App. No. 17190066.5, dated Jan. 16, 2018.
European Search Report for App. No. 17190084.8, dated Feb. 9, 2018.
European search report for App. No. 19219612.9, dated Apr. 29, 2020.
European Search Report for App. No. 20198933.2, dated Dec. 22, 2020.
F. Locatelli, et al: "Haemodialysis with on-line monitoring equipment: tools or toys?" Nephrology Dialysis Transplantation., vol. 20, No. 1, Jan. 1, 2005.
First Examination Report for India Patent Application No. 201714028051, dated May 27, 2021.
Heiko Hickstein, Et Al; "Clinical application of fuzzy-controlled blood pressure stabilization in patients prone to hypotension duirng hemodiaylsis", Dyalysis & Transplantation, vol. 38, No. 2, Feb. 1, 2009, pp. 58-64.
Henderson, et al, "Online Preparation of Sterile Pyrogen-Free Electrolyte Solution," Trans. Am. Soc. Artif.Intern.Organs, 1978 pp. 465-467.
Indian OA of Nov. 21, 2019 in 2981/KOLNP/2013.
International Preliminary Report on Patentability for App. No. PCT/US2019/019334, dated Jun. 12, 2019.
International Search Report for App. No. PCT/US2019/061670, dated Jan. 15, 2020.
Laurent, Jeanpierre, "Continuous Monitoring of Dynamic Systems: Application to Monitoring of Dialyzed Patients" Oct. 30, 2004, received from internet: http://laurent.jeanpierre1.free.fr/recherche/papiers/aista2004.pdf.
Office Action for EP App. No.17185808.7, dated Oct. 8, 2019.
Office Action for European App. No. 17718241.7, dated Apr. 2, 2020.
Office Action for European Application No. 17185636.2, dated Mar. 19, 2020.
Office Action in Chinese App. No. 201710778666.3 dated Sep. 19, 2019.
Office Action in Chinese App. No. 201780019238.0, dated Sep. 25, 2020.
PCT/US2016/058579 International Search Report dated Jan. 31, 2017.
PCT/US2016/058579 Written Opinion dated Jan. 31, 2017.
PCT/US2017/025868 International Search Report dated Jun. 29, 2017.
PCTUS2017025876 International Search Report dated Jun. 29, 2017.
PCTUS2017025876 Written Opinion dated Jun. 29, 2017.
Second Chinese Office Action for Application No. 201811107614.4, dated Apr. 15, 2021.
Wollenstein, et al, "Colorimetric gas sensors for the detection of ammonia, nitrogen dioxide, and carbon monoxide: current status and research trends", Sensor and Test Conference 2011, Jan. 2, 2011, pp. 562-567.

* cited by examiner

DEXTROSE CONCENTRATION SENSOR FOR A PERITONEAL DIALYSIS SYSTEM

CROSS REFERENCE

This application claims priority to application Ser. No. 15/478,562, filed Apr. 4, 2017, which claims priority to provisional App. No. 62/318,169, filed Apr. 4, 2016; application Ser. No. 15/478,569, filed Apr. 4, 2017, which claims priority to provisional App. No. 62/318,173, filed Apr. 4, 2016; application Ser. No. 15/478,576, filed Apr. 4, 2017, which claims priority to provisional App. No. 62/318,183, filed Apr. 4, 2016; application Ser. No. 17/187,256, filed Feb. 26, 2021, which is a continuation of application Ser. No. 15/666,614, filed Aug. 2, 2017, which claims priority to App. No. 62/373,133, filed Aug. 10, 2016; application Ser. No. 15/673,487, filed Aug. 10, 2017, which claims priority to App. No. 62/373,225, filed Aug. 10, 2016; and application Ser. No. 17/024,039, filed Sep. 17, 2020, which is a continuation of application Ser. No. 15/666,631, filed Aug. 2, 2017, which claims priority to App. No. 62/373,228, filed Aug. 10, 2016.

FIELD

Systems, methods, and devices for sensing dextrose concentration of peritoneal dialysate infused into and removed from a patient during treatment. The systems and methods include sensors, processors, and flow paths for determining dextrose concentrate of the peritoneal dialysate.

BACKGROUND

Osmotic agent concentrations are necessary for a Peritoneal Dialysis (PD) exchange or cycle. A mismatch of PD prescription with membrane transport properties can lead to underdialysis and/or inadequate therapy. Improper PD prescriptions can also lead to higher risk of death or quicker transfer to Hemodialysis (HD). The osmotic agent prescription for peritoneal dialysis regimen is based on an understanding of a patient's membrane transport function, daily required small solute removal, and residual kidney function (RKF). For example, a patient with a membrane having a fast solute transfer rate matched with a PD prescription with a long dwell can result in volume overload and result in higher mortality and increased risk of hospitalization. To avoid unnecessary osmotic agent exposure, a PD regimen can be designed to reach UF targets with solutions of lowest osmolality.

During online generation of the peritoneal dialysate at the patient's home or in a clinical setting, accurate generation of the peritoneal dialysate fluid requires that the dextrose powder is properly proportioned and completely dissolved or reconstituted with the injection quality water. The dextrose powder is initially reconstituted with the injection quality water to form a concentrate solution. However, available systems and methods that generate PD fluid online require the ability to confirm complete dissolution and homogeneity of the dextrose concentrate solution and ability to confirm accurate proportioning of dextrose solution to meet the pharmacopoeia requirement of +/−5% of the treatment prescription.

Hence, there is a need for systems and methods for determining fluid characteristics of a peritoneal dialysate prior to infusing into a patient, during infusion or in an effluent or filtrate removed from the patient. The need extends to systems and methods monitoring the fluid characteristics during any phase of treatment. The need further includes either directly or indirectly measuring an amount of an osmotic agent such as dextrose used in peritoneal dialysate. The need further includes either directly or indirectly measuring an amount of an osmotic agent used during a treatment session. The need still further includes determining specific fluid characteristics of a peritoneal dialysate removed from a patient. The need includes mechanisms to determine whether dextrose or other osmotic agent is mixed uniformly in a concentrate. The need still further includes monitoring fluid proportioning of an osmotic agent to generate a suitable peritoneal dialysate. The need includes monitoring an osmotic agent or dextrose concentration at a suitable precision and accuracy for use in a peritoneal dialysate.

SUMMARY

The first aspect of the disclosure relates to a sensor. In any embodiment, the sensor can include a transmitter light source operable to emit light through a fluid flow path; and an optical receiver operable to receive at least a portion of the light emitted by the transmitter light source, passing through the fluid flow path, wherein the sensor can be configured to measure at least one optical parameter of a fluid in the fluid flow path in one or more wavelengths.

In any embodiment, the at least one optical parameter can be an index of refraction of light passing through the fluid in the fluid flow path.

In any embodiment, the index of refraction of light passing through the fluid in the fluid flow path can be in a wavelength range of 780 nm to 2500 nm.

In any embodiment, the transmitter light source can be a visible point light source, and the optical receiver can be a charge-coupled device (CCD) camera, wherein an angle of bend of the light when passed through the fluid in the fluid flow path can be proportional to the refractive index of the fluid.

In any embodiment, the sensor can include an optical fiber defining a first end and a second end, wherein at least a portion of the optical fiber between the first end and the second end can be disposed within the fluid flow path, wherein the transmitter light can be optically couplable to the first end of the optical fiber and the optical receiver can be optically couplable to the second end of the optical fiber.

In any embodiment, the at least a portion of the optical fiber disposed within the fluid flow path includes an etched portion.

In any embodiment, the transmitter light can be an infrared transmitter light emitting diode and the optical receiver can be an infrared receiver photodiode In any embodiment, the optical fiber forms part of a disposable fluid path cassette.

In any embodiment, the fluid includes a dextrose fluid flow.

The features disclosed as being part of the first aspect of the disclosure can be in the first aspect of the disclosure, either alone or in combination.

The second aspect of the disclosure can be drawn to a peritoneal dialysis system. In any embodiment, the system can include a dextrose source fluidly connectable to a peritoneal dialysis fluid generation flow path; at least one refractive index sensor; a control system programmed to receive a refractive index from the at least one refractive index sensor and to determine a dextrose concentration of a fluid in the peritoneal dialysis fluid generation flow path based on the refractive index.

In any embodiment, the system can include a temperature sensor in communication with the control system, wherein the control system can be programmed to determine the dextrose concentration of the fluid in the peritoneal dialysis fluid generation flow path based on the refractive index and a temperature of the fluid in the peritoneal dialysis fluid generation flow path.

In any embodiment, the control system further programmed to generate an alert if a dextrose concentration in the peritoneal dialysis fluid flow path can be outside of a predetermined range.

In any embodiment, the system can include a fluid manifold disposed between the dextrose source and a catheter, the fluid manifold fluidically coupled to the peritoneal dialysis fluid generation flow path, wherein the at least one refractive index sensor can be positioned to emit light through the fluid manifold, the control system programmed to receive a refractive index from the at least one refractive index sensor and to determine a dextrose concentration of a fluid in fluid manifold based on the refractive index.

In any embodiment, at least a portion of the at least one refractive index sensor can be disposed in the fluid manifold.

In any embodiment, the control system can be programmed to at least one of: direct fluid into the peritoneal dialysis fluid generation flow path if the dextrose concentration in the fluid manifold can be within a predetermined range; and direct fluid into a drain line if the dextrose concentration in the fluid manifold can be outside of a predetermined range.

In any embodiment, the control system can be programmed to determine at least one of: a peritoneum infection level based on the dextrose concentration in the fluid manifold; and a treatment effectiveness based on the dextrose concentration in the fluid manifold.

The features disclosed as being part of the second aspect of the disclosure can be in the second aspect of the disclosure, either alone or in combination.

The third aspect of the disclosure can be drawn to a method of using the peritoneal dialysis system. In any embodiment, the method can include the steps of adding water to a dextrose source to generate a dextrose concentrate, wherein the dextrose source initially contains solid dextrose; using the dextrose concentrate to generate a peritoneal dialysis fluid; measuring a refractive index of the peritoneal dialysis fluid; and determining a dextrose concentration in the peritoneal dialysis fluid based on the refractive index to determine if the dextrose concentration can be within a predetermined range.

In any embodiment, the method can include the step of determining whether the solid dextrose can be fully dissolved and uniformly mixed based on the dextrose concentration of the dextrose concentrate.

The features disclosed as being part of the third aspect of the disclosure can be in the second aspect of the disclosure, either alone or in combination.

The fourth aspect of the disclosure can be drawn to a method of using the peritoneal dialysis system. In any embodiment, the method can include the steps of measuring a refractive index of a peritoneal dialysis fluid prior to infusing the peritoneal dialysis fluid into a patient; and determining a dextrose concentration of the peritoneal dialysis fluid based on the refractive index.

In any embodiment, the method can include the step of infusing the peritoneal dialysis fluid into the patient if the dextrose concentration can be within a predetermined range.

The features disclosed as being part of the fourth aspect of the disclosure can be in the second aspect of the disclosure, either alone or in combination.

The fifth aspect of the disclosure can be drawn to a method of using the peritoneal dialysis system. In any embodiment, the method can include the steps of measuring a refractive index in a fluid drained from a peritoneal cavity of a patient; and determining a dextrose concentration of the fluid drained from the peritoneal cavity of the patient.

In any embodiment, the method can include the step of determining at least one of a peritoneum infection level based on the dextrose concentration in the fluid and a treatment effectiveness based on the dextrose concentration in the fluid.

The features disclosed as being part of the fifth aspect of the disclosure can be in the second aspect of the disclosure, either alone or in combination.

DETAILED DESCRIPTION

Figure 1:
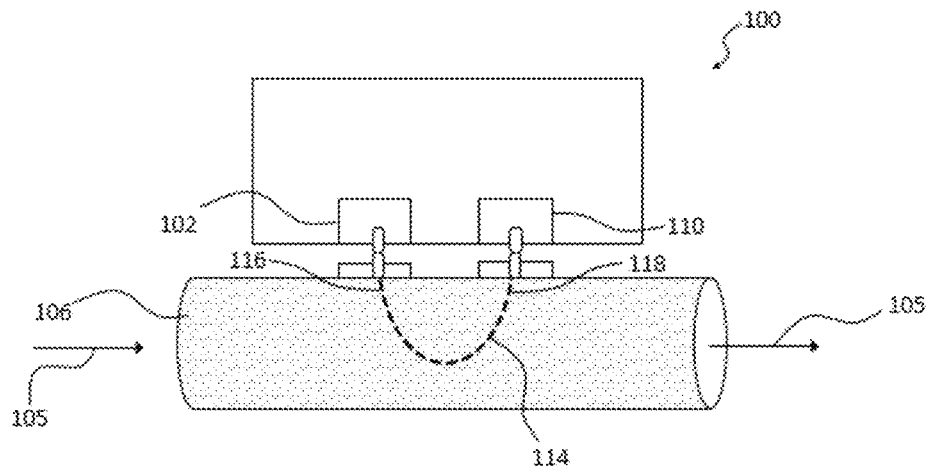
FIG. 1 shows a dextrose sensor for sensing fluid characteristics of peritoneal dialysate in a peritoneal dialysate generation flow path.

Unless defined otherwise, all technical and scientific terms used generally have the same meaning as commonly understood by one of ordinary skill in the art.

The articles "a" and "an" are used to refer to one or to over one (i.e., to at least one) of the grammatical object of the article. For example, "an element" means one element or over one element.

"Activated carbon" refers to a form of carbon processed to have small pores, increasing the surface area available for adsorption.

The term "angle of bend of light" refers to the angle at which the light bends relative to normal when passing through a medium.

The term "cassette" refers to a generally geometric case or cartridge that can be easily loaded or unloaded or coupled to another component.

The term "catheter" refers to a flexible tube inserted through a narrow opening into a body cavity.

The term "charge-coupled device (CCD) camera" refers to image capture technology employing a variety of charge-coupled device (CCD) detector configurations, wherein a CCD is an integrated circuit containing an array of linked, or coupled, capacitors.

The term "combined peritoneal dialysate effluent line and infusion line" refers to a fluid connector for delivering and removing fluid from a peritoneal cavity of a patient. The combined infusion and effluent line can optionally be separated into an independent infusion line and an independent effluent line.

The term "comprising" includes, but is not limited to, whatever follows the word "comprising." Use of the term indicates the listed elements are required or mandatory but that other elements are optional and may be present.

The terms "communication" and "communicating" refer to an electronic or wireless link between two components.

A "concentrate pump" is a pump configured to move fluid between a concentrate source and a flow path.

A "concentrate solution" is a solution of one or more solutes in water. The concentrate solution can have a solute concentration greater than that to be used in dialysis.

A "concentrate source" is a source of one or more solutes. The concentrate source can have one or more solutes that has a solute concentration greater than the solute concentration to be used for dialysis. The concentrate in the concentrate source can also be lower than the solute concentration generally used in dialysis for generation of low concentration dialysate The terms "concentration" and "solute concentration" refers to an amount of a solute dissolved in a given amount of a solvent.

A "conductivity sensor" is device for measuring the electrical conductance of a solution and/or the ion, such as a sodium ion, concentration of a solution.

The term "consisting of" includes and is limited to whatever follows the phrase "consisting of" The phrase indicates the limited elements are required or mandatory and that no other elements may be present.

The term "consisting essentially of" includes whatever follows the term "consisting essentially of" and additional elements, structures, acts, or features that do not affect the basic operation of the apparatus, structure or method described.

The terms "control," "controlling," or "controls" refers to the ability of one component to direct the actions of a second component.

A "control system" can be a combination of components acting together to maintain a system to a desired set of performance specifications. The control system can use processors, memory and computer components configured to interoperate to maintain the desired performance specifications. The control system can also include fluid or gas control components, and solute control components as known within the art to maintain the performance specifications.

The terms "controlled addition," to "control addition," or "controlling addition" refer to the ability to add one or more substances or fluids to a flow path or container in an accurately controllable amount.

The term "detachable" relates to any component of that can be separated from a system, module, cartridge, or any component. "Detachable" can also refer to a component that can be taken out of a larger system with minimal time or effort. In certain instances, the components can be detached with minimal time or effort, but in other instances can require additional effort. The detached component can be optionally reattached to the system, module, cartridge, or other component.

The terms "determining" and "determine" refer to ascertaining a particular state of a system or variable(s).

The term "dextrose source" refers to a source of dextrose in solid and/or solution form. The dextrose source can interface with at least one other module found in systems for dialysis. The dextrose source can contain at least one fluid pathway and include components such as conduits, valves, filters, or fluid connection ports, any of which are fluidly connectable to each other or to a fluid flow path. The dextrose source can either be formed as a stand-alone enclosure or a compartment integrally formed with an apparatus for dialysis for containing a dextrose source.

The term "dialysate" describes a fluid into or out of which solutes from a fluid to be dialyzed diffuse through a membrane. Dialysate can differ depending on the type of dialysis to be carried out. For example, dialysate for peritoneal dialysis may include different solutes or different concentrations of solutes than dialysate for hemodialysis.

A "dialysate container" can be any container capable of storing or containing dialysate for dialysis. The container any be of any suitable, size, geometry, or configuration.

The term "downstream" refers to a position of a first component in a flow path relative to a second component wherein fluid will pass by the second component prior to the first component during normal operation. The first component can be said to be "downstream" of the second component, while the second component is "upstream" of the first component.

A "drain line" can be a fluid line for carrying fluid to a drain such as a waste receptacle or drain. The drain line can be connected to a peritoneal cavity of a patient for draining fluid.

The term "effluent line" refers to a fluid connector for removing fluid from a peritoneal cavity of a patient. The term "effluent line" can also refer to a combined effluent and infusion line.

The term "etched portion" refers to a portion of a component that has been subjected to an etching process to produce a thinning of material to form a pattern, or design on the material by eating into the material's surface, such as through the use of an acid or laser beam.

The term "filter" refers to a porous component through which fluid can pass, but that traps one or more materials within the fluid.

A "flow meter" can be a device capable of measuring an amount or rate of fluid moving past or through a particular location.

The term "flow sensor" refers to any component capable of measuring a volume or a rate of fluid moving through a conduit.

The term "fluid" can be any substance without a fixed shape that yields easily to external pressure such as a gas or a liquid. Specifically, the fluid can be water containing any solutes at any concentration. The fluid can also be dialysate of any type including fresh, partially used, or spent.

A "fluid characteristic" can be any sensed characteristic of a fluid, including temperature, pressure, concentration, color, or any other characteristic.

The term "fluid flow path" refers to a path of a fluid subjected to unbalanced forces.

The term "fluid manifold" refers to a device capable of carrying a fluid that connects multiple inputs or outputs and provides for the flow of the fluid therethrough.

The terms "fluid connection," "fluidly connectable," "fluidically engage", "fluidically coupled" or "fluidly connected" refer to the ability to pass fluid or gas from one point to another point. The two points can be within or between any one or more of compartments, modules, systems, and components, all of any type.

The terms "to generate peritoneal dialysate" or "peritoneal dialysate generation" refers to creating a peritoneal dialysate solution from constituent parts.

A "heater" can be a component capable of raising the temperature of a substance, container, or fluid.

The terms "heating" or to "heat" refer to raising the temperature of a substance, fluid, or container.

The term "index of refraction" can be a numerical measure to which no physical dimension is assigned, that describes how fast light travels through a material. The refractive index determines how much the path of light is bent, or refracted, when entering the material.

The term "infrared receiver photodiode" refers to a semiconductor device that is coupleable to an optical fiber that converts light into an electrical current.

The term "infrared transmitter light emitting diode" refers to a solid-state light-emitting (SSL) device that produces and transmits radiant energy that is invisible to the human eye, wherein the Infrared wavelengths are longer than visible light but shorter than radio waves.

An "integrated cycler" is a component for movement of fluid into and out of the peritoneal cavity of a patient, wherein the integrated cycler forms a part of an overall system. For example, the integrated cycler can be contained in a housing with other components used for peritoneal dialysis and be in fluid and electrical connection with desired components.

The term "infusing" or to "infuse" a fluid refers to the movement of peritoneal dialysate into the peritoneal cavity of a patient.

An "infusion line" is a fluid line for carrying peritoneal dialysate into a body cavity or part of a patient such as a peritoneal cavity. The term "infusion line" can also refer to a combined effluent and infusion line.

The term "input/output interface" refers to a module of a processor or computing system that allows data to be received by the processor or computing system and provided by the processor or computing system. The input/output interfaces can automatically receive and provide data from sensors, or can receive data manually input through the interface, such as by a keyboard.

An "integrated cycler" is a component for movement of fluid into and out of the peritoneal cavity of a patient, wherein the integrated cycler forms a part of an overall system. For example, the integrated cycler can be contained in a housing with other components used for peritoneal dialysis and be in fluid and electrical connection with desired components.

An "ion concentrate" refers to one or more ionic compounds. The ion concentrate can have one or more ionic compounds in the ion concentrate. Further, the ion concentrate can have an ion concentration greater than an ion concentration to be used in dialysis.

An "ion concentrate source" refers to a source of one or more ionic compounds. The ion concentrate source can be in water or solid form. The ion concentrate source can further have one or more ionic compounds that are at a higher ion concentration greater than generally used in dialysis.

The term "level of sterility" refers to an estimated probability of viable organisms surviving a sterilization process.

The term "machine-readable storage medium" refers to any electronic device capable of storing information in a digital format for reading by a computer, processor, or other electronic device.

The term "microbial filter" refers to a device inhibiting passage of microbes or fragments of microbes such as endotoxins in a fluid or solution while allowing the passage of the fluid or solution.

A "nanofilter" is a filter membrane having nanometer sized pores.

The term "optical fiber" refers to a glass (silica) or plastic tubular structure providing a means to transmit light between the two ends of the fiber. The fiber is typically flexible and transparent.

The terms "optical fiber cable" and "fiber-optic cable" refer to an assembly containing one or more optical fibers.

A "optical fitting feature" is any protrusion, indentation, groove, ridge, having any shape, size, or geometry that ensures that only a corresponding fitting feature complementary to the fitting feature can form a connection or fit to the corresponding fitting feature. The fitting feature can also include non-mechanical means for ensuring complementary connection such as magnets placed at particular locations, or visual or aural indicators such as color, lettering, or sound. The fitting feature can be affixed, integral, or labeled on a component or surface to ensure a corresponding feature on a desired component or surface can mate or connect to the component or surface having the fitting feature.

The term "optical parameter" is any parameter of a material, including the refractive index, reflection, or any other characteristic that defines how the material interacts with light.

The term "optical receiver" or "fiber optic receiver" refers to a component that is configured to receive pulses of emitted light that are sent through optical fibers into electrical signals.

The term "optically coupled" or "optically coupleable" refers to the positioning of a plurality of light sources, or a light source and an optic receiver in a manner to align the light passing therethrough.

An "osmotic agent" is a substance dissolved in water capable of driving a net movement of water by osmosis across a semi-permeable membrane due to concentration differences of the osmotic agent on each side of the semi-permeable membrane.

An "osmotic agent source" refers to a source of osmotic agents in solid and/or solution form. The osmotic agent source can interface with at least one other module found in systems for dialysis. The osmotic agent source can contain at least one fluid pathway and include components such as conduits, valves, filters, or fluid connection ports, any of which are fluidly connectable to each other or to a fluid flow path. The osmotic agent source can either be formed as a stand-alone enclosure or a compartment integrally formed with an apparatus for dialysis for containing an osmotic agent source.

A "patient" or "subject" is a member of any animal species, preferably a mammalian species, optionally a human. The subject can be an apparently healthy individual, an individual suffering from a disease, or an individual being treated for a disease.

The term "peritoneal cavity" refers to the space between the parietal peritoneum and visceral peritoneum of a patient.

"Peritoneal dialysate" or "peritoneal dialysis fluid" is a dialysis solution to be used in peritoneal dialysis having specified parameters for purity and sterility. Peritoneal dialysate is not the same as dialysate used in hemodialysis although peritoneal dialysate may be used in hemodialysis.

A "peritoneal dialysate generation flow path" is a path used in generating dialysate suitable for peritoneal dialysis.

A "peritoneal dialysate generation system" refers to a collection of components used to generate peritoneal dialysate.

"Peritoneal dialysis" is a therapy wherein a dialysate is infused into the peritoneal cavity, which serves as a natural dialyzer. In general, waste components diffuse from a patient's bloodstream across a peritoneal membrane into the dialysis solution via a concentration gradient. In general, excess fluid in the form of plasma water flows from a patient's bloodstream across a peritoneal membrane into the dialysis solution via an osmotic gradient. Once the infused peritoneal dialysis solution has captured sufficient amounts of the waste components the fluid is removed. This cycle can be repeated for several cycles each day or as needed.

The term "peritoneal dialysis cycler" or "cycler" refers to components for movement of fluid into and out of the peritoneal cavity of a patient, with or without additional components for generating peritoneal dialysate or performing additional functions.

The term "peritoneal infection" refers to the introduction of an organism into the otherwise sterile peritoneal environment, such as viruses, bacteria, fungi, and parasites.

The term "predetermined range" refers to a range of acceptance that was determined by previous events or people rather than by chance.

The term "pierceable septum" refers to a component through which a needle or syringe can be inserted to draw fluid out of a flow path.

The term "portion of fluid" refers to an amount of a fluid less than the entire amount of the fluid in a flow path, container, or reservoir.

The term "positioned" refers to the location of a component.

A "predetermined time" is a set time for an event to occur, such as a set time of day, or a set length of time from a previous event.

The term "prescribed solute concentration" refers to a chosen concentration of one or more solutes in peritoneal dialysate based on patient needs and intended for use by a patient.

The term "pressure sensor" refers to a device for measuring the pressure of a gas or liquid in a vessel, container, or fluid line.

The term "processor" is a broad term and is to be given its ordinary and customary meaning to a person of ordinary skill in the art. The term refers without limitation to a computer system, state machine, and/or processor designed to perform arithmetic or logic operations using logic circuitry that responds to and processes the basic instructions that drive a computer. In any embodiment of the first, second, third, and fourth invention, the terms can include ROM ("read-only memory") and/or RAM ("random-access memory") associated therewith.

The term "pump" refers to any device that causes the movement of fluids or gases by applying suction or pressure.

The terms "pumping," "pumped," or to "pump" refers to moving or flowing a fluid using a pump of any type known to those of ordinary skill in the art.

The terms "pumping fluid" or to "pump fluid" refer to moving a fluid through a flow path with a pump.

A "purified water source" is a water source containing purified water.

"Purified water" can be defined as water produced by distillation, deionization, reverse osmosis, or other suitable processes and meets the definition of "purified water" in the United States Pharmacopeia, 23d Revision, Jan. 1, 1995, and the FDA at 21 CFR Section § 165.110(a)(2)(iv). Other criteria for purified water can be determined by those of skill in the art, particularly as relating to purified water suitable for peritoneal dialysis.

The term "receiving" or to "receive" means to obtain information from any source.

The term "refractive index" refers to the ratio of the speed of light through a fluid to the speed of light through water.

A "refractive index sensor" is any component capable of detecting the ratio of the speed of light through a fluid to the speed of light through water. The concentration of one or more solutes in the fluid can be determined based on the refractive index.

The term "removing" fluid refers to flowing fluid out of a container, system, or patient.

A "reverse osmosis module" is a set of components to drive fluid through one or more semipermeable membranes, wherein pressure is used to move the fluid from a side of the semipermeable membrane with a higher concentration of one or more solutes to a side of the semipermeable membrane with a lower concentration of the one or more solutes.

A "sensor" is a component capable of determining one or more states of one or more variables in a system.

A "selected time" is a set time chosen by a user or algorithm.

A "sensor" is a component capable of determining one or more states of one or more variables in a system.

A "solute" is a substance dissolved in, or intended to be dissolved in, a solvent, such as water.

The term "sorbent cartridge" refers to a cartridge containing one or more sorbent materials for removing specific solutes from solution. The term "sorbent cartridge" does not require the contents in the cartridge be sorbent based, and the contents of the sorbent cartridge can be any contents capable of removing solutes from a dialysate. The sorbent cartridge may include any suitable amount of one or more sorbent materials. In certain instances, the term "sorbent cartridge" refers to a cartridge which includes one or more sorbent materials besides one or more other materials capable of removing solutes from dialysate. "Sorbent cartridge" can include configurations where at least some materials in the cartridge do not act by mechanisms of adsorption or absorption.

A "sterilization module" is a component or set of components to sterilize a fluid by removing or destroying chemical or biological contaminants.

The term "storing" or to "store" refers to saving electronic data or information in a machine readable medium.

A "temperature sensor" is a sensor capable of determining the temperature of a fluid.

The term "transmitter light source" refers to a component capable of producing and transmitting radiant energy that is invisible to the human eye.

The term "transmitting" or to "transmit" refers to sending information electronically.

The term "treatment effectiveness" refers to the likelihood that a treatment protocol will benefit patients in a clinical population when administered in clinical practice.

An "ultrafilter" is a semi permeable membrane through which a fluid can pass with removal of one or more solutes or particles from the fluid.

The term "upstream" refers to a position of a first component in a flow path relative to a second component wherein fluid will pass by the first component prior to the second component during normal operation. The first component can be said to be "upstream" of the second component, while the second component is "downstream" of the first component.

A "user interface" is a component that allows a user to communicate information or instructions to a processor or a memory device and to receive information or instructions from the processor or memory device.

A "UV light source" is a component which uses ultraviolet light to kill biological contaminants in a fluid.

A "valve" is a device capable of directing the flow of fluid or gas by opening, closing, or obstructing one or more pathways to allow the fluid or gas to travel in a path. One or more valves configured to accomplish a desired flow can be configured into a "valve assembly."

The term "visible point light source" refers to a component capable of emitting light from a single identifiable localized source.

The term "volume" refers to an amount of a fluid.

The term "water purification module" refers to a component or components capable of removing biological or chemical contaminants from water.

A "waste reservoir" is a container for collecting and storing used or waste fluids.

The term "water source" refers to a source from which potable water can be obtained.

Dextrose Concentration Sensor for a Peritoneal Dialysis System

FIG. 1 illustrates an optical sensor 100 for use in a peritoneal dialysis system. In any embodiment, the optical sensor 100 can be a refractive index sensor. The optical sensor 100 measures dextrose or other osmotic agent concentration in a fluid 105, and more particularly, a peritoneal dialysate fluid, prepared for infusion, undergoing infusing and/or removed from a patient undergoing peritoneal dialysis treatment. In any embodiment, the optical sensor 100 enables intermittent or continuous measure of a dextrose concentration in a reconstituted dextrose concentrate, such as that in a bolus of peritoneal dialysate fluid. In any embodiment, the optical sensor 100 may provide for a measure of dextrose in a fresh peritoneal dialysate fluid and/or a spent peritoneal dialysate fluid during patient treatment with high accuracy. For example, the optical sensor 100 may aid in providing information so as to know when to exchange the dialysate fluid. When the peritoneal dialysate fluid is in the peritoneum, glucose will be absorbed into the patient and water will be draw into the peritoneum due to osmotic pressure. These effects will cause the refractive index of the fluid to decrease due to reduced fluid density. This effect will be partially offset by transport of other solutes into the peritoneum due to diffusion. At some point the fluid will be equilibrated with the patient and the refractive index change should decrease or stop, signaling the fluid should be exchanged. The combined effect of glucose, water and other solutes would be measured, with the change in refractive index vs. time a useful signal to know when the peritoneal dialysis fluid is no longer effectively exchanging and needs to be changed. In any embodiment, the optical sensor 100 may further provide for calculation and thus monitoring, of a patient's dextrose level during the peritoneal dialysis treatment.

In any embodiment, the optical sensor 100 measures one or more optical parameters, for example the refractive index of light passing through the fresh peritoneal dialysate fluid prior to infusion, during infusion and/or the spent peritoneal dialysate fluid. In any embodiment, a direct correlation between the concentration of dextrose and the measured refractive index of the dextrose solution, and more particularly the peritoneal dialysate fluid can be determined. In some embodiments, the optical sensor 100 can be configured to measure the refraction of light emitted in one or more wavelengths in a range of 700 nm-2.5 mm, for example in a range of 780-2500 nm, or any intermediate, smaller, or larger wavelength range.

Figure 2:
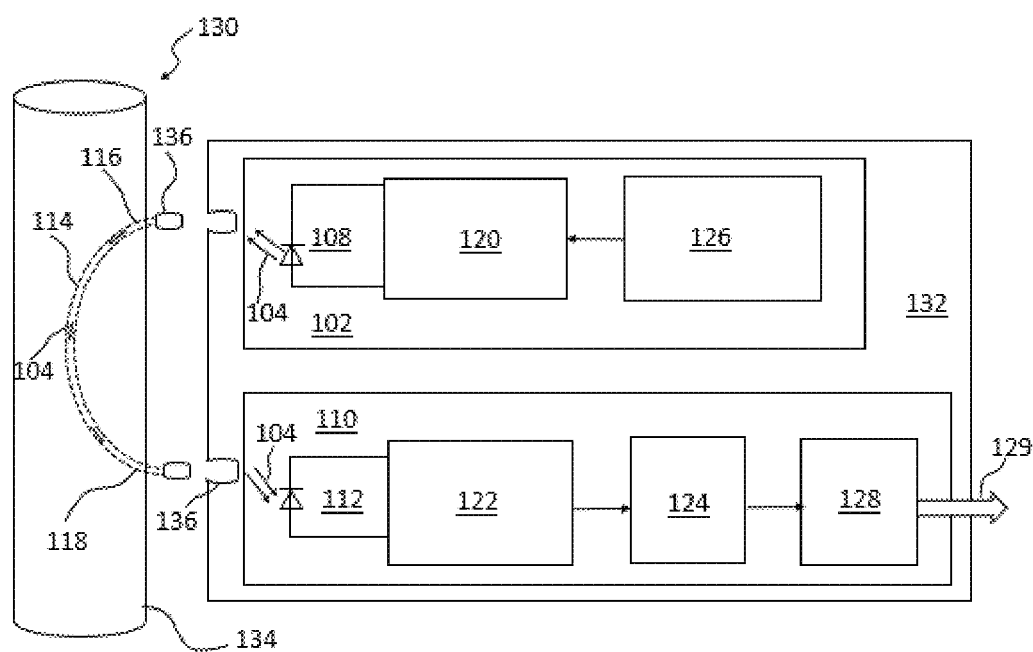
FIG. 2 is a block diagram of the dextrose sensor of FIG. 1, for sensing fluid characteristics of a peritoneal dialysate in a peritoneal dialysate generation flow path.

As shown in FIG. 1 and FIG. 2, the optical sensor 100 can have a transmitter light source 102. The transmitter light source 102 can be operable to emit light 104 through the fluid 105 in a fluid flow path 106. In any embodiment, the transmitter light source 102 can be an infrared light emitting diode (LED) 108, configured to emit light, and more specifically infrared light, in one or more wavelengths in a range of 780-2500 nm. The optical sensor 100 further has an optical receiver, also referred to herein as a fiber optic receiver, 110 operable to receive at least a portion of the light 104 emitted by the transmitter light source 102, passing through the fluid flow path 106. In any embodiment, the optical receiver 110 can be a photodiode 112, configured to receive the emitted light 104. The transmitter light source 102 and the optical receiver 110 are optically coupled to an optical fiber 114, providing for the passage therethrough of the light 104 emitted by the transmitter light source 102, for receipt by the optical receiver 110. The optical fiber 114 defining a first end 116 that is optically coupled to the transmitter light source 102 and a second end 117 that is optically coupled to the optical receiver 110. In an embodiment, a plurality of optical fibers may be used to form an optical fiber cable defining a first end that is optically coupled to the transmitter light source 102 and a second end that is optically coupled to the optical receiver 110.

Referring more specifically to FIG. 2, in any embodiment the optical sensor 100 may also have an LED driver 120 capable of driving the infrared LED 108 with a 40 KHz signal to produce the emitted light 104 modulated at 40 KHz. A high gain, low noise, trans-impedance amplifier (TIA) 122, amplifies the portion of the 40 KHz light 104 received by the photodiode 112 to the order of $10^6$. The amplified signal is passed through a 40 KHz low pass filter (LPF) 124. A 40 KHz oscillator 126 and the 40 KHz LPF 124 enables the optical sensor 100 to detect only a 40 KHz signal emitted by the photodiode 112 and thus immune to ambient light conditions. A filtered output voltage is proportional to the attenuation of light in the optical fiber 114. The LPF output is converted to digital signal 129 using analog to digital converter 128 which can be read by a microcontroller/microprocessor (not shown) of the peritoneal dialysis system.

In the illustrated embodiment, the optical sensor 100 is configured as a disposable cassette-like component that is optically coupled or "plugged" into the light emitting/processing equipment, encompassing the previously described light generating/receiving components, generally referenced 132. In any embodiment, the optical fiber 114 can be formed as part of the fluid flow path 106, and more particularly, is formed as part of a disposable manifold 134 that in combination form the disposable fluid path cassette 130. The transmitter light source 102, including the IR transmitter LED 108, and the optical receiver 110, including the IR receiver photodiode 112, are formed as part of the light emitting/processing equipment 132. During operation, the disposable fluid path cassette 130 can be optically coupled to the light emitting/processing equipment 132 in a manner to achieve optical alignment of the optical fiber 114 with a respective IR transmitter LED 108 and IR receiver photodiode 112. A plurality of optical fitting feature 136, capable of cooperative engagement, to achieve such optical coupling are illustrated disposed on the first and second ends 116, 118 of the optical fiber 114 and the light emitting/processing equipment 132. The optical fiber 114 can be configured detachable from the light emitting/processing equipment 132. In any embodiment, the disposable manifold 134 can be configured to fluidically engage with a peritoneal dialysate fluid line (presently described with regard to FIG. 6). For example, a direct connection to the peritoneal dialysate fluid line can use any type of connector known in the art. The connectors can be single-use or reusable connectors and should provide for sterile flow of the peritoneal dialysate between the fluid line and the manifold 134. The connectors should preferably be closed connectors, to avoid contact between the fluids and the external environment. The connectors can be single use or disposable connectors that provide transfer of sterile fluids.

Figure 3:
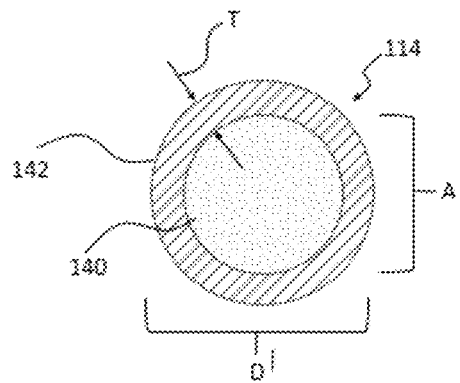
FIG. 3 shows a cross-section of an optical fiber of the dextrose sensor of FIG. 1, for sensing fluid characteristics of a peritoneal dialysate in a peritoneal dialysate generation flow path.

Referring now to FIG. 3, in any embodiment, a diameter "D" of the optical fiber 114 can be in a range of 920-1040 microns, for example in a range of 940 mm-1020 microns, or any intermediate, smaller, or larger diameter range. In any embodiment, a preferred diameter "D' of the optical fiber 114 can be 1000 microns. In any embodiment, the optical fiber 114 can be formed as a cladding etched plastic optical fiber (POF), and more particularly, includes a core material 140 encompassed therein a cladding material 142. In any embodiment, the core material 140 may be formed of a polymeryl-methacrylate resin. In any embodiment, the core material 140 has a refractive index of 1.49 and/or a numerical aperture "A" of 0.5. In any embodiment, the cladding material 142 may be formed of a fluorinated polymer. Thin cladding thickness "T" (<3 microns) can facilitate interaction between the light 104 that is guided through the optical fiber 114 and the peritoneal dialysate fluid into which the fiber is disposed, thus resulting in a strong optical response to refractive index changes in the peritoneal dialysate fluid. The optical fiber 114 may be a single mode fiber or a multi-mode fiber.

Figure 4:
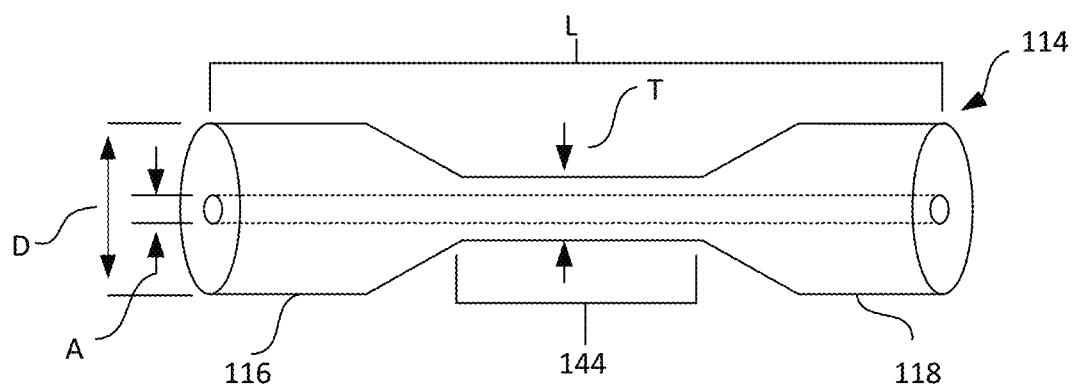
FIG. 4 shows an etched portion of an optical fiber of a dextrose sensor for sensing fluid characteristics of a peritoneal dialysate in a peritoneal dialysate generation flow path.

Referring now to FIG. 4, the optical fiber 114 may include an etched portion 144 disposed between the first end 116 and the second end 118 and extending along at least a portion of a length "L" of the optical fiber 114. In any embodiment, the etched portion 144 can be defined by a portion of the optical fiber 114 that has been subjected to an etching process to produce a thinning of material by eating into the material's surface, such as through the use of an acid or laser beam. The etched portion 144 provides for bending of the optical fiber 114 into a U-shape for disposal within the fluid flow path 106. In an embodiment, the optical fiber 114 has a bend radius of 8 mm±0.05 mm. The attenuation of emitted light 104 by the optical sensor 100 shows linear power variation with respect to refractive index of the fluid, and more particularly, the peritoneal dialysate fluid the light is disposed in.

Figure 5:
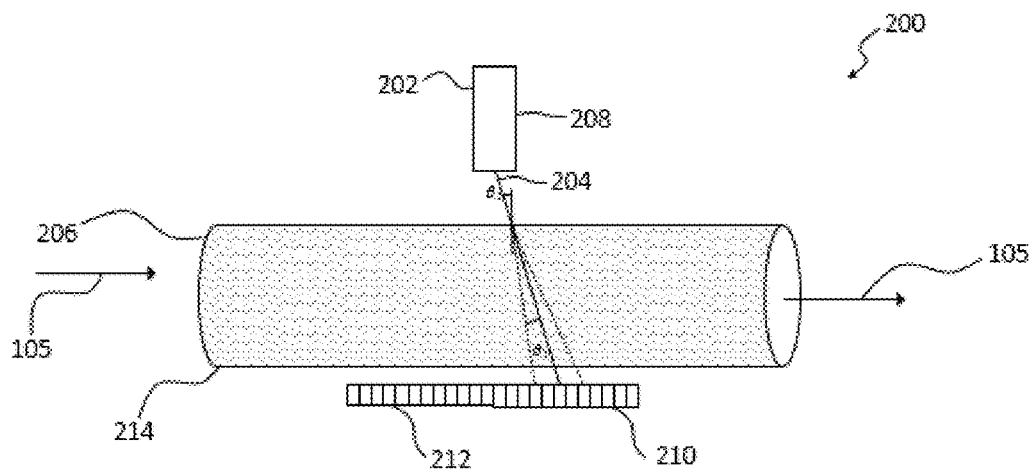
FIG. 5 shows an alternative of a dextrose sensor for sensing fluid characteristics of a peritoneal dialysate in a peritoneal dialysate generation flow path.

FIG. 5 illustrates an alternate embodiment of an optical sensor 200 for use in a peritoneal dialysis system (described presently). One of skill will understand that features of the optical sensor 200 that have been previously described with regard to the embodiment of FIGS. 1-4 will be referenced in FIG. 5 having the same reference number. The optical sensor 200 may be somewhat similar to the optical sensor 100, and thus a detailed description will be omitted for the sake of brevity as to like features.

Similar to optical sensor 100 of the first embodiment, the optical sensor 200 measures dextrose or other osmotic agent concentration in a fluid 105, and more particularly, a peritoneal dialysate fluid, prepared for infusion, undergoing infusing and/or removed from a patient undergoing peritoneal dialysis treatment. In any embodiment, the optical sensor 200 enables intermittent or continuous measure of a dextrose concentration in a reconstituted dextrose concentrate, such as that in a bolus of peritoneal dialysate fluid. The optical sensor 200 may provide for a measure of dextrose in a fresh peritoneal dialysate fluid and/or a spent peritoneal dialysate fluid during patient treatment with high accuracy. In any embodiment, the optical sensor 200 may further provide for calculation and thus monitoring, of a patient's dextrose level during the peritoneal dialysis treatment.

The optical sensor 200 measures one or more optical parameters, for example the refractive index of light passing through the fresh peritoneal dialysate fluid prior to infusion or during infusion and/or the spent peritoneal dialysate fluid. In some embodiments, the optical sensor 200 can be configured to measure the refraction of light emitted in one or more wavelengths in a range of 700 nm-2.5 mm, for example in a range of 780-2500 nm, or any intermediate, smaller, or larger wavelength range.

The optical sensor 200 can have a transmitter light source 202. The transmitter light source 202 can be operable to emit light 204 through a transparent fluid flow path 206. In any embodiment, the transmitter light source 202 can be a visible point light source 208, such as a laser, or the like, configured to emit infrared or near-infrared light in one or more wavelengths in a range of 780-2500 nm. The optical sensor 200 can also have an optical receiver 210 operable to receive at least a portion of the light 204 emitted by the transmitter light source 202, passing through the transparent fluid flow path 206. In any embodiment, the optical receiver 210 can be a charge-coupled device (CCD) camera 212, or an array of array of CCD sensors, configured to receive the emitted light 204. The transmitter light source 202 and the optical receiver 210 are optically aligned, providing for the passage therethrough of the light 204 emitted by the transmitter light source 202 to be received by the optical receiver 210.

In FIG. 5, the fluid flow path 206, and more particularly, the manifold 214 can be made of a light transparent material to provide for the passage of emitted light 204 therethrough. The manifold 214 can be configured generally similar to that previously described with the first embodiment, such as in a manner to provide for fluidic coupling to the peritoneal dialysate fluid line. The light 204 emitted by the transmitter light source 202 when passed through the fluid 105, and more particularly the peritoneal dialysate fluid, within the manifold 204 can be bent with the angle of bend directly proportional to the refractive index of the fluid 105. Based on the angle of refraction, the emitted light ray falls at different points on the CCD camera. By measuring the distance at which the light 105 incidents on the optical receiver 210, angle $\theta_1$ can be calculated. The angle of incidence and $n_1$ of the light transparent manifold 214, provides for the refractive index $n_2$ to be calculated using Snell's law which states $n_1 \sin \theta_1 = n_2 \sin \theta_2$. The measure of refractive index gives indirect measurement of the amount of dextrose dissolved in the fluid 105.

Figure 6:
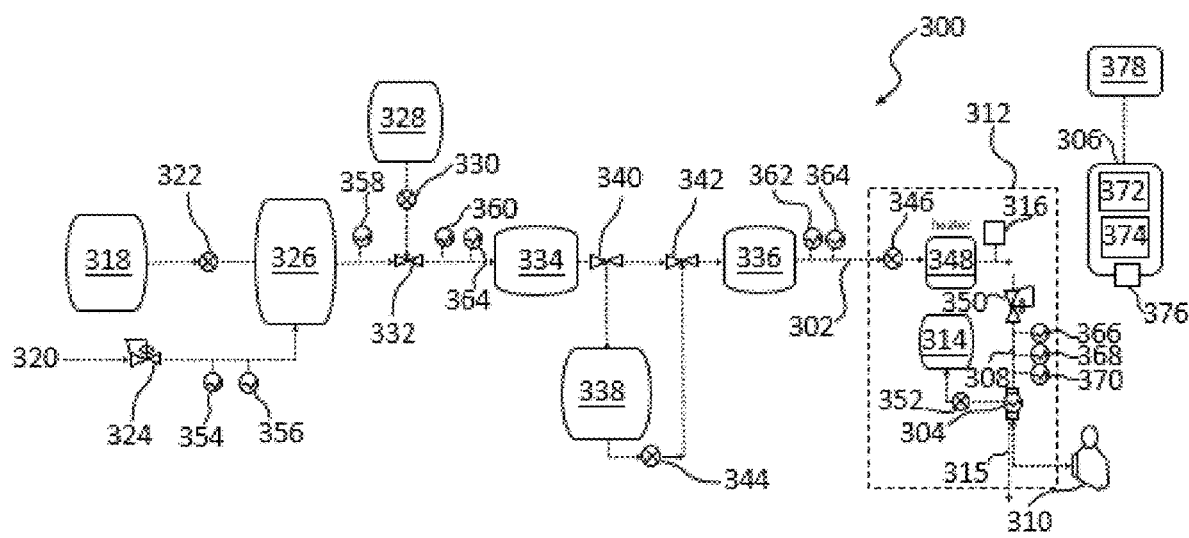
FIG. 6 shows a peritoneal dialysate generation flow path including a dextrose sensor for sensing fluid characteristics of a peritoneal dialysate in a peritoneal dialysate generation flow path.

FIG. 6 illustrates a peritoneal dialysis system 300 for sensing a dextrose concentration of a peritoneal dialysate fluid in the peritoneal dialysis system 300, incorporating an optical sensor as previously described. The system 300 defines a peritoneal dialysate generation flow path 302, at least one optical sensor 304, such as sensor 100 or 200 previously described and also referred to as a refractive index sensor, and a control system 306. The control system 306 can be programmed to receive a refractive index from the at least one refractive index sensor 304 and determine a dextrose concentration of the peritoneal dialysate fluid in the peritoneal dialysate generation flow path 302. The system 300, as illustrated, includes a combined peritoneal dialysate effluent line and infusion line, referred to herein as peritoneal dialysate fluid line 308. The peritoneal dialysate fluid line 308 can be in fluid communication with a catheter (not shown) having a single channel used for both filling and removal of the peritoneal dialysate fluid from a peritoneal cavity of a patient 310. One of skill in the art will understand that separate effluent and infusion lines can be used. The system 300 can be configured to direct the peritoneal dialysate fluid to the peritoneal dialysate fluid line 308 and patient 310 if the dextrose concentration in the fluid manifold 134 (FIGS. 1-2 and 5) is within a predetermined range and direct the peritoneal dialysate fluid into a drain line 315 if the dextrose concentration in the fluid manifold is outside of a predetermined range and unusable.

The system 300 can be embodied as a manual peritoneal dialysis system or an automated system including an integrated peritoneal dialysis cycler 312 wherein the peritoneal dialysis cycler 312 includes the peritoneal dialysate fluid line 308, a portion of the peritoneal dialysate generation flow path 302, and the at least one refractive index sensor 304 for sensing a dextrose concentration of the peritoneal dialysate fluid in the peritoneal dialysis system 300. Alternatively, the peritoneal dialysis cycler 312 can be nonintegrated with the peritoneal dialysate generation flow path 302, whereby the peritoneal dialysate can be prepared off-line and provided to the cycler 312. In an alternate embodiment, the system may operate manually and not include a cycler. The control system 306 can be a separate device in communication with the at least one refractive index sensor 304 or can be a part of the peritoneal dialysis cycler 312, whether integrated or nonintegrated.

The peritoneal dialysate fluid line 308 can be fluidly connected to a waste reservoir 314 to collect effluent peritoneal dialysate fluid. Optionally, a diverted flow path, such as the drain line 315, can be in fluid communication with the peritoneal dialysate fluid line 308 for analysis of the peritoneal dialysate fluid outside of the peritoneal dialysis cycler 312 and/or directing of the peritoneal dialysate fluid into a drain line 315 if the dextrose concentration in the fluid manifold is outside of a predetermined range. A valve (not shown) in the cycler 312 can divert fluid from the peritoneal dialysate fluid line 308 to the drain line 315 to provide determination of fluid characteristics of the peritoneal dialysate fluid outside of the cycler 312 continuously or at specific intervals and in predetermined amounts.

A pump (not shown) can provide an additional driving force for moving peritoneal dialysate through the diverted flow path. A similar analysis can be conducted on the generated peritoneal dialysate by diverting a volume of generated peritoneal dialysate into the diverted path (not shown). Analysis of the generated peritoneal dialysate can serve as a quality check on the newly generated peritoneal dialysate, as well as calibration of the refractive index sensor 304 by comparing sensed values to known values of the dialysate. Analysis of the newly generated dialysate can also be used by the system for self-learning or machine learning to adjust the dialysate composition to a precision beyond the capabilities of known systems. Analysis of the generated peritoneal dialysate can also be used as a safety system to ensure the concentration of solutes in the peritoneal dialysate is within a predetermined threshold of the expected values.

Alternatively, or additionally, the system 300 can include a sampling port 316. The sampling port 316 can be fluidly connected to the peritoneal dialysate fluid line 308. The sampling port 316 can alternatively be fluidly connected to the diverted flow path. The sampling port 316 can be covered by a pierceable septum. A user can insert a needle or syringe through the pierceable septum to draw out a portion of the peritoneal dialysate in the peritoneal dialysate fluid line 308 or diverted flow path. The pierceable septum can re-seal after removal of the needle or syringe to avoid contamination of the peritoneal dialysate.

When used with the integrated cycler 312, the peritoneal dialysate generation flow path 302 can further include a water source, such as a water tank 318, one or more water purification modules 326, a concentrate source 328, a sterilization module, such as one or more filters 334 and/or UV light source 336, and the peritoneal dialysis cycler 312. The water source 318, the water purification module 326, the concentrate source 328, the sterilization module 334, 336, and peritoneal dialysis cycler 312 can be fluidly connectable to the peritoneal dialysate generation flow path 302. The peritoneal dialysate generation flow path 302 can be fluidly connected to the peritoneal dialysate fluid line 308 to infuse peritoneal dialysate into the peritoneal cavity of the patient 310.

In an alternate embodiment, either additionally, or as an alternative to a water tank 318, the system 300 can use a direct connection to a water source 320. A system pump 322 can control the movement of fluid through the peritoneal dialysate generation flow path 302. If a direct connection to a water source 320 is used, a pressure regulator 324 can ensure that an incoming water pressure is within a predetermined range. The water source 320 can be a non-purified water source, such as tap water, wherein the water from the water source 320 can be purified by the system. A non-purified water source can provide water without additional purification, such as tap water from a municipal water source, water that has undergone some level of purification, but does not meet the definition of "purified water" provided, such as bottled water or filtered water. The water source can contain water meeting the WHO drinkable water standards provided in Guidelines for Drinking Water Quality, World Health Organization, Geneva, Switzerland, 4th edition, 2011. Alternatively, the water source 320 can be a source of purified water, meaning water that meets the applicable standards for use in peritoneal dialysis without additional purification.

The system pumps the fluid from water source 318 or 320 through a water purification module 326 to remove chemical contaminants in the fluid in preparation for creating the peritoneal dialysate. The system pumps water from the water source to a water purification module to remove chemical contaminants in the fluid in preparation of the dialysate. The water purification module 326 can be a sorbent cartridge containing anion and cation exchange resins and/or activated carbon.

After the fluid passes through the water purification module 326, the fluid can be pumped to a concentrate source 328, where necessary components for carrying out peritoneal dialysis can be added from the concentrate source 328. The concentrate source 328 can contain one or more solutes for generating the peritoneal dialysate from purified water. In an embodiment, the concentrate source 328 can be a dextrose concentrate source containing solid dextrose, wherein adding water to the dextrose solute generates the dextrose concentrate.

The one or more solutes in the concentrate source 328 are utilized to create a peritoneal dialysis fluid that matches a dialysis prescription. A concentrate pump 330 and concentrate valve 332 in communication with the processor or computing unit control the movement of concentrates from the concentrate source 328 to the peritoneal dialysate generation flow path 302 in a controlled addition. Alternatively, the concentrate valve 332 can be a hose T or backflow restricting hose T. The concentrates added from the concentrate source 328 to the peritoneal dialysate generation flow path 302 can include components required for use in peritoneal dialysate. One of skill in the art will understand that any number of concentrate sources can be used, each containing concentrates of one or more substances. For example, the concentrate sources 328 can include any number of concentrates combined or in separate concentrate sources. One or more osmotic agent sources can be included in addition to a single ion concentrate source. Alternatively, multiple ion concentrate sources can be used with each ion concentrate in a separate concentrate source. Any combination of concentrates in any number of concentrate sources can be used. One desired outcome can be to provide a concentration for a particular ion that is lower than a patient's pre-dialysis ion concentration. Additionally, if multiple ion sources are to be delivered by a concentrate source, the present system can control each component concentration independent of the other components. Hence, the present disclosure can avoid adjusting down every ion insofar as an added diluent may adversely affect concentrations of ions already in a normal range.

Upon addition of solutes from the concentrate source 328, the fluid in the peritoneal dialysate generation flow path 302 can contain all the necessary solutes for peritoneal dialysis. The peritoneal dialysate should reach a level of sterility for peritoneal dialysis such that patients will not contract an infection due to bacteria or other pathogens in fluid used for peritoneal dialysate. The system 300 can pump the fluid to a sterilization module for sterilizing the peritoneal dialysate prior to infusion into the patient 310. As shown in FIG. 6, the sterilization module can include one or more of a filter 334 and a UV light source 336, or any combination thereof. In any embodiment, the sterilization module filter 334 can include a microbial filter, nanofilter, or any filter device inhibiting passage of microfibers or fragments of microbes such as endotoxins in the peritoneal dialysate while allowing the passage of the peritoneal dialysate. In any embodiment, the UV light source 336 can be positioned at any location in the peritoneal dialysate generation flow path 302, including upstream of the filter 334, downstream of the filter 334, or disposed between multiple filters in a multi-filter system. The sterilization module can be any component or set of components capable of sterilizing the peritoneal dialysate.

The generated peritoneal dialysate can be pumped directly to the integrated cycler 312 for immediate infusion into a patient 310. Alternatively, the dialysate can be pumped to an optional dialysate container 338 as a pre-prepared bolus of solution for storage until ready for use by a patient 310. A plurality of valves 340, 342 can control the movement of fluid to either the dialysate container 338 or the integrated cycler 312. Stored dialysate in dialysate container 338 can be pumped as needed to back into the peritoneal dialysate generation flow path 302 by a pump 344 through valve 342. The dialysate container 338 can store enough peritoneal dialysate for a single infusion of peritoneal dialysate into the patient 310, or enough peritoneal dialysate for multiple or continuous infusions into one or multiple patients.

In an embodiment, the generated peritoneal dialysate can be pumped to a valve (not shown) that can control movement of the peritoneal dialysate to multiple flow options. The peritoneal dialysate can be pumped to the integrated cycler 312 or diverted for use with a nonintegrated external cycler (not shown) or to a dialysate container (not shown). All various pumping/diversion options can be performed contemporaneously or selectively. Alternative valve and pump configurations for performing the same functions are contemplated by the present invention. For example, a direct connection to an external cycler can use any type of connector known in the art. The connectors can be single-use or reusable connectors and should provide for sterile transfer of fluids. The connectors should preferably be closed connectors, to avoid contact between the fluids and the external environment.

The integrated cycler 312 can include a metering pump 346 for metering peritoneal dialysate into the peritoneal cavity of the patient 310. A heater 348 heats the peritoneal dialysate to a desired temperature prior to infusion into the patient 310. A pressure regulator 350 ensures the peritoneal dialysate pressure can be within a predetermined range safe for infusion into the patient 310. The metering pump 346 can use any safe pressure for infusing fluid into the patient 310. Generally, the pump pressures are on average set at ±10.3 kPa or 77.6 mmHg. If there is no fluid flow, the maximum pressure can increase to ±15.2 kPa or 113.8 mmHg for a short period, such as less than 10 seconds. The peritoneal dialysate can be infused into the peritoneal cavity of the patient 310 through the fluid line 308. After a dwell period, the peritoneal dialysate can be drained from the patient 310 through the fluid line 308, or a separate effluent line (previously described). A pump 352 provides a driving force for removing the peritoneal dialysate from the patient 310. The optional waste reservoir 314 can be included to store the used peritoneal dialysate for disposal. Alternatively, the peritoneal dialysate fluid line 308 can be directly connected to the drain line 315 for direct disposal. The waste reservoir 314 can be any size, including between 12 and 20 L. For patients requiring a higher drainage, a drain manifold can be included for connecting multiple waste reservoirs.

In addition to the refractive index sensor 304, various additional sensors may be positioned in the peritoneal dialysis system 300 ensure that one or more fluid characteristics of the generated peritoneal dialysate fluid can be within predetermined parameters. The sensors can be fluidly connected to one or more of the peritoneal dialysate generation flow path 302 and the peritoneal dialysate fluid line 308. The one or more sensors can be separate sensors or one or more combined sensors. In an embodiment, one or more sensors can be external to the peritoneal dialysis cycler 312. The system an also include duplication of analysis with duplicated sensors in multiple locations. Duplication of the analysis allows calibration of the sensors and acts as a safety check to ensure the sensors are properly functioning. The duplicated sensors can be attached to the cycler 312 or in a standalone system.

The sensors may include a flow meter 354 to ensure the incoming water is at a correct flow rate, while a pressure sensor 356 can ensure the incoming water is at an appropriate pressure. A conductivity sensor 358 can be used to ensure that the water exiting the water purification module 326 has been purified to a level safe for use in peritoneal dialysis. A conductivity sensor 360 can ensure the conductivity of the dialysate after the addition of concentrates from concentrate source 328 is within a predetermined range. A pH sensor 362 can ensure the pH of the peritoneal dialysate is within a predetermined range. After passing through the sterilization module including UV light source 336, a pH sensor 362 and a conductivity sensor 364 can be used to ensure that no changes in the pH or conductivity have occurred during purification or storage of the dialysate in the dialysate container 338. The integrated cycler 312 includes the refractive index sensor 304, as described previously, to ensure that the concentration of dextrose, or other osmotic agents in the peritoneal dialysate is within a predetermined range. The integrated cycler 312 further may include a flow meter 366, a pressure sensor 368 and a temperature sensor 370 to ensure that the dialysate being infused into the patient 310 is within a proper flow rate, pressure, and temperature range. One of skill in the art will understand that alternative or additional sensing methods can be used, and any sensor or method known in the art can be incorporated.

The control system 306 can include the one or more processors 372, memory 374, and one or more input/output interfaces 376. One of ordinary skill in the art will recognize that the memory 374 can include long-term memory and operating memory, and/or memory serving as both long-term memory and operating memory. The memory 374 can be a machine-readable storage medium. The memory 374 can be in communication with the processor 372 and store instructions that when executed perform any of the methods of the present disclosure. The input/output interface(s) 376 can include an input port to receive information from the one or more sensors, and an output interface to output data to a user, such as an alert notification 378 regarding the sensed data. The processor 372 can be in communication with the sensors and store data received from the at least one sensor in the memory 374. As with all features of the present application, intervening components, such as the input/output interface 376, can be present between the processor 372 and the one or more sensors. The control system 306 can be a stand-alone device independent of the peritoneal dialysis cycler 312 or can be a part of the peritoneal dialysis cycler 312. The control system 306 can be a remote device in network communication with the one or more sensors, such as via the internet. In an embodiment, the dialysis system 300 can include a user interface (not shown) in communication with the control system 306, allowing the patient 310 to direct one or more functions of the system, such as the generation of peritoneal dialysate at a selected time.

Figure 7:
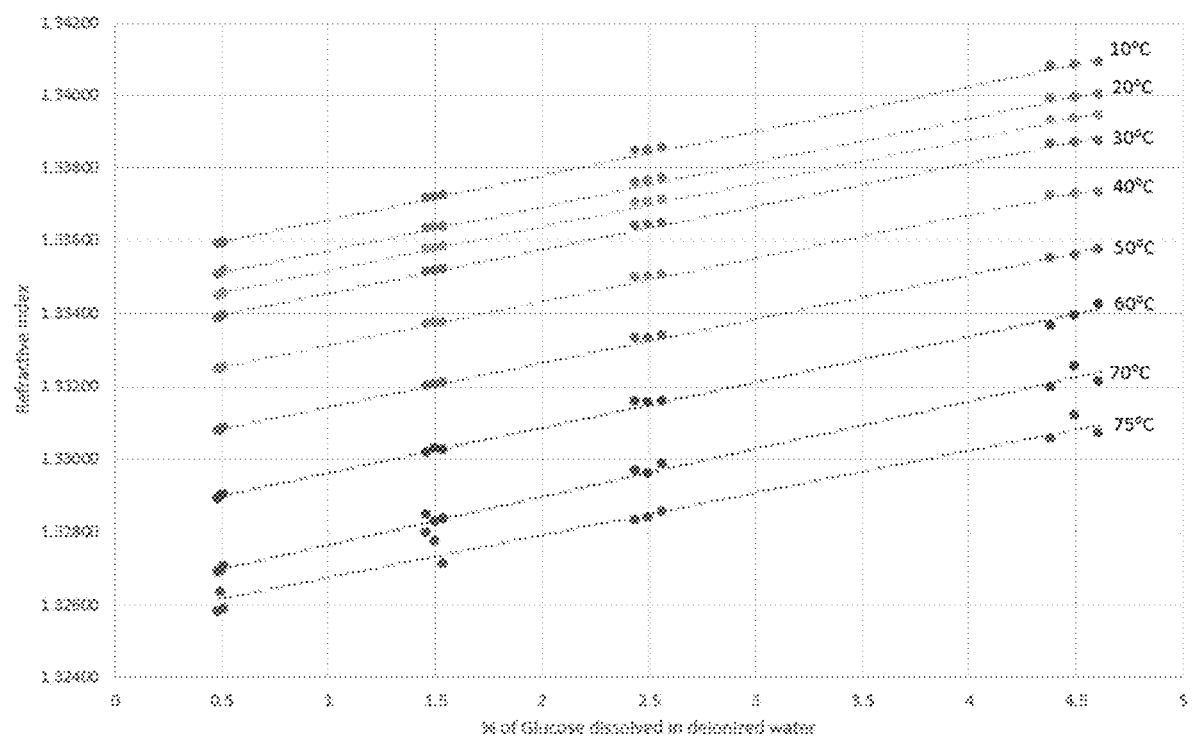
FIG. 7 illustrates lab measurements done on fluid prepared with different solid dextrose concentrations at different fluid temperature.

FIG. 7 illustrates lab measurements done on fluid prepared with different solid dextrose concentrations at different fluid temperature. In this example, the y-axis is refractive index, and the x-axis is percentage (%) glucose dissolved in deionized water. The measurements show that the refractive index increases linearly with the dextrose concentration at a given constant temperature. The measurements also show that the refractive index decreases linearly with increase in temperature. The measured refractive index values are then compensated for temperature using the fluid temperature data measured by a temperature sensor in the system. Temperature compensated refractive index values are used to confirm concentration of dissolved the dextrose in the solution. As evidenced by the graph, the refractive index measured by the optical sensor is directly proportional to the dextrose concentration in the concentrate or the proportioned PD fluid.

The disclosed refractive index sensor and peritoneal dialysis system incorporating the refractive index sensor can measure the concentration of dextrose in a dialysate fluid line prior to infusion, during infusion or as effluent subsequent to the infusion process. Solute concentrate in the dialysate can measured subsequent to the addition of the solute to the purified water to determine adequate mixing of the solute prior to infusion. Membrane transfer efficiency can also be calculated by measuring changes in solute concentration of the dialysate at multiple times during the dwell period. Concentrations of solutes measured at multiple times during the dwell period can also be used to determine the presence of a peritoneum infection level, treatment effectiveness and the optimal time to end a peritoneal dialysis cycle. One skilled in the art will understand that various combinations and/or modifications and variations can be made in the systems and methods depending upon the specific needs for operation. Features illustrated or described as being part of an aspect can be used in the aspect, either alone or in combination.

What is claimed is:

1. A peritoneal dialysis system, comprising:
   A dextrose source fluidly connectable to a peritoneal dialysis fluid generation flow path;
   A cycler configured to deliver a fluid from the peritoneal dialysis fluid generation flow path to a patient, wherein at least a portion of the peritoneal dialysis fluid generation flow path is disposed within the cycler;
   At least one refractive index sensor disposed within the cycler and configured to measure the refractive index of the fluid in the peritoneal dialysis fluid generation flow path, the refractive index sensor including:
      A transmitter light source, the transmitter light source operable to emit a light through the peritoneal dialysis fluid generation flow path;
      An optical receiver, the optical receiver operable to receive at least a portion of the light emitted by the transmitter light source and passing through the peritoneal dialysis fluid generation fluid flow path; and
      An optical fiber defining a first end and a second end, wherein at least a portion of the optical fiber between the first end and the second end is disposed within the peritoneal dialysis fluid generation flow path;
      Wherein the transmitter light source is optically couplable to the first end of the optical fiber and the optical receiver is optically couplable to the second end of the optical fiber; and
   A control system, wherein the control system is programmed to receive a refractive index from the at least one refractive index sensor and to determine a dextrose concentration of the fluid in the peritoneal dialysis fluid generation flow path based on the refractive index.

2. The system of claim 1, further comprising a temperature sensor in communication with the control system, the control system programmed to determine the dextrose concentration of the fluid in the peritoneal dialysis fluid generation flow path based on the refractive index and a temperature of the fluid in the peritoneal dialysis fluid generation flow path.

3. The system of claim 1, the control system further programmed to generate an alert if the dextrose concentration in the peritoneal dialysis fluid flow path is outside of a predetermined range.

4. The system of claim 1, further comprising a fluid manifold disposed between the dextrose source and a catheter, the fluid manifold fluidically coupled to the peritoneal dialysis fluid generation flow path, wherein the at least one refractive index sensor is positioned to emit light through the fluid manifold, the control system programmed to receive the refractive index from the at least one refractive index sensor and to determine the dextrose concentration of a fluid in fluid manifold based on the refractive index.

5. The system of claim 4, wherein at least a portion of the at least one refractive index sensor is disposed in the fluid manifold.

6. The system of claim 4, wherein the control system is programmed to at least one of:

direct fluid into the peritoneal dialysis fluid generation flow path if the dextrose concentration in the fluid manifold is within a predetermined range; and direct fluid into a drain line if the dextrose concentration in the fluid manifold is outside of the predetermined range.

7. The system of claim 4, wherein the control system is programmed to determine at least one of:

a peritoneum infection level based on the dextrose concentration in the fluid manifold; and a treatment effectiveness based on the dextrose concentration in the fluid manifold.

8. The system of claim 1, wherein the transmitter light source is a visible point light source and the optical receiver is a charge-coupled device (CCD) camera, wherein an angle of bend of the light when passed through the fluid in the peritoneal dialysis fluid generation flow path is proportional to the refractive index of the fluid in the peritoneal dialysis fluid generation flow path.

9. The system of claim 1, wherein at least a portion of the optical fiber disposed within the peritoneal dialysis fluid generation flow path includes an etched portion.

10. The system of claim 1, wherein the optical fiber forms part of a disposable fluid path cassette.

11. The system of claim 1, wherein the transmitter light is an infrared transmitter light emitting diode and the optical receiver is an infrared receiver photodiode.

12. A method using the system of claim 1, comprising the steps of:

adding water to a dextrose source to generate a dextrose concentrate, wherein the dextrose source initially contains solid dextrose;

using the dextrose concentrate to generate a peritoneal dialysis fluid;

measuring a refractive index of the peritoneal dialysis fluid; and determining a dextrose concentration in the peritoneal dialysis fluid based on the refractive index to determine if the dextrose concentration is within a predetermined range.

13. The method of claim 12, further comprising the step of determining whether the solid dextrose is fully dissolved and uniformly mixed based on the dextrose concentration of the dextrose concentrate.

14. A method using the system of claim 1, comprising the steps of:

measuring a refractive index of a peritoneal dialysis fluid prior to infusing the peritoneal dialysis fluid into a patient; and determining a dextrose concentration of the peritoneal dialysis fluid based on the refractive index.

15. The method of claim 14, further comprising the step of infusing the peritoneal dialysis fluid into the patient if the dextrose concentration is within a predetermined range.

* * * * *